(12) United States Patent
Imamura et al.

(10) Patent No.: US 11,445,990 B2
(45) Date of Patent: Sep. 20, 2022

(54) ROUNDING IMAGING MANAGEMENT APPARATUS, METHOD FOR OPERATING ROUNDING IMAGING MANAGEMENT APPARATUS, PROGRAM FOR OPERATING ROUNDING IMAGING MANAGEMENT APPARATUS, DATA STRUCTURE, AND RECORDING APPARATUS

(71) Applicant: FUJIFILM Corporation, Tokyo (JP)

(72) Inventors: Ryo Imamura, Kanagawa (JP); Kazuhiro Makino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 257 days.

(21) Appl. No.: 16/799,807

(22) Filed: Feb. 24, 2020

(65) Prior Publication Data

US 2020/0281547 A1 Sep. 10, 2020

(30) Foreign Application Priority Data

Mar. 4, 2019 (JP) .............................. JP2019-038837

(51) Int. Cl.
*G01N 23/04* (2018.01)
*A61B 6/00* (2006.01)
(Continued)

(52) U.S. Cl.
CPC ............ *A61B 6/4208* (2013.01); *A61B 6/563* (2013.01); *G06T 1/0007* (2013.01); *G06T 7/0012* (2013.01); *G06T 2207/10124* (2013.01)

(58) Field of Classification Search
CPC ..... A61B 6/4208; A61B 6/563; A61B 6/4405; A61B 5/447; A61B 5/746; A61B 5/743;
(Continued)

(56) References Cited

U.S. PATENT DOCUMENTS

2008/0292168 A1* 11/2008 Winkelmann ......... G16H 30/20
382/238
2013/0272502 A1* 10/2013 Watanabe ................ H05G 1/26
378/98
(Continued)

FOREIGN PATENT DOCUMENTS

EP 3660859 A1 * 6/2020 ........... A61B 5/1123
JP 2015006433 1/2015
(Continued)

OTHER PUBLICATIONS

Office Action of Japan Counterpart Application, with English translation thereof, dated Jan. 18, 2022, pp. 1-6.
(Continued)

*Primary Examiner* — Irakli Kiknadze
(74) *Attorney, Agent, or Firm* — JCIPRNET

(57) ABSTRACT

A CPU of a rounding imaging management apparatus functions as a first acquisition unit, a second acquisition unit, a creation unit, and an output controller. The first acquisition unit acquires imaging order information indicating content of radiography in the rounding imaging to be performed. The second acquisition unit acquires, from time results data in which a necessary time in the rounding imaging performed in the past is registered, the necessary time. The creation unit creates a rounding plan of the rounding imaging on the basis of the imaging order information and the necessary time. The output controller performs a control for outputting the rounding plan.

18 Claims, 39 Drawing Sheets

(51) Int. Cl.
*G06T 7/00* (2017.01)
*G06T 1/00* (2006.01)

(58) Field of Classification Search
CPC ... A61B 5/1115; A61B 5/7435; A61B 5/6898; A61B 5/7264; A61B 5/002; A61B 5/6892; A61B 5/0077; A61B 5/1117; A61B 2562/0219; A61B 6/06; A61B 6/4035; A61B 6/4441; A61B 6/5211; A61B 6/5235; A61B 6/5229; A61B 6/547; A61B 6/4452; A61B 6/4283; A61B 6/10; A61B 6/542; A61B 6/501; A61B 6/469; A61B 6/4476; A61B 6/14; A61B 6/03; A61B 6/035; A61B 6/032; A61B 6/4266; A61B 6/4233; A61B 6/548; A61B 6/5241; A61B 6/488; A61B 6/5217; A61B 6/545; A61B 5/1123; A61B 6/56; G06T 1/0007; G06T 7/0012; G06T 2207/10124; G06T 11/006; G06T 7/30; G06T 5/50; G06Q 10/047; G16H 40/63; G16H 40/20; G16H 40/67; G16H 50/20; G16H 50/30; G21K 1/046; G01N 23/18; G01N 23/04; G01N 2223/646; G01N 2223/3303; H05G 1/26; H05G 1/02; G03B 42/04; H04N 5/32; A61G 7/08; G01C 21/206; G07C 9/38

USPC ........................................................ 378/62
See application file for complete search history.

(56) References Cited

U.S. PATENT DOCUMENTS

| | | | | |
|---|---|---|---|---|
| 2013/0336445 | A1* | 12/2013 | Sehnert | G01N 23/044 378/42 |
| 2014/0219524 | A1* | 8/2014 | Takeguchi | G16H 50/30 382/128 |
| 2016/0058402 | A1* | 3/2016 | Okuno | A61B 6/4405 378/193 |
| 2018/0344272 | A1* | 12/2018 | Nakamura | A61B 6/461 |

FOREIGN PATENT DOCUMENTS

| | | |
|---|---|---|
| JP | 2017099783 | 6/2017 |
| JP | 2018158026 | 10/2018 |

OTHER PUBLICATIONS

"Office Action of Japan Counterpart Application" with English translation thereof, dated Jul. 19, 2022, p. 1-p. 8.

* cited by examiner

IMAGING ORDER INFORMATION —14

| ORDER ID | PATIENT ID | NAME | HOSPITAL ROOM INFORMATION | IMAGING TECHNIQUE | ... |
|---|---|---|---|---|---|
| OD001 | P0001 | FUJI TARO | ROOM 201 | SIMPLE IMAGING, CHEST FRONT LYING POSITION | ... |
| OD002 | P0005 | ASHIGARA HANAKO | ROOM 203 | SIMPLE IMAGING, ABDOMINAL FRONT LYING POSITION | ... |
| OD003 | P0008 | KAISEI KAZUO | ROOM 204 | SIMPLE IMAGING, NECK SIDE LYING POSITION | ... |
|  |  |  | ⋮ |  |  |

IMAGING TIME RESULTS DATA —70

| PATIENT ID | IMAGING TECHNIQUE | IMAGING SLOT | IMAGING TIME |
|---|---|---|---|
| P0001 | SIMPLE IMAGING, CHEST FRONT LYING POSITION | 10:00 TO 10:14 | 5 MINUTES |
| | | 10:00 TO 10:29 | 5 MINUTES |
| | | 10:00 TO 10:44 | 10 MINUTES |
| | | ⋮ | |
| | | 13:00 TO 13:14 | 10 MINUTES |
| | | ⋮ | |
| | SIMPLE IMAGING, ABDOMINAL FRONT LYING POSITION | 10:00 TO 10:14 | 8 MINUTES |
| | | ⋮ | |
| P0002 | SIMPLE IMAGING, CHEST FRONT LYING POSITION | 10:00 TO 10:14 | 7 MINUTES |
| | | ⋮ | |
| P0003 | SIMPLE IMAGING, THIGH SIDE SITTING POSTURE | 10:00 TO 10:14 | 15 MINUTES |
| | | ⋮ | |
| | SIMPLE IMAGING, THIGH BACK LYING POSITION | 10:00 TO 10:14 | 12 MINUTES |
| | | ⋮ | |
| P0004 | SIMPLE IMAGING, CHEST FRONT LYING POSITION | 10:00 TO 10:14 | 10 MINUTES |
| | | ⋮ | |
| ⋮ | | | |

| DEPARTURE PLACE | TRANSIT PLACE | ARRIVAL PLACE | TIME SLOT | MOVEMENT TIME |
|---|---|---|---|---|
| PREPARATION ROOM | HALLWAY A2 | ROOM 201 | 10:00 TO 10:14 | 1.5 MINUTES |
| | | | 10:15 TO 10:29 | 1.5 MINUTES |
| | | | 10:30 TO 10:44 | 2 MINUTES |
| | | | ... | |
| | | | 13:00 TO 13:14 | 1.5 MINUTES |
| PREPARATION ROOM | HALLWAY A2 | ROOM 202 | 10:00 TO 10:14 | 2 MINUTES |
| ROOM 208 | HALLWAY B2, ELEVATOR HALL A2, ELEVATOR A, ELEVATOR HALL A3, HALLWAY A3 | ROOM 301 | 10:00 TO 10:14 | 8 MINUTES |
| | | | 10:15 TO 10:29 | 4 MINUTES |
| | | | 10:30 TO 10:44 | 5 MINUTES |
| | | | ... | |
| | | | 13:00 TO 13:14 | 5 MINUTES |
| ... | | | | |

TT

71 — IMAGING TIME RESULTS DATA

FIG. 24

ROOM OCCUPANCY STATUS INFORMATION — 92

| PATIENT ID | ROOM OCCUPANCY STATUS | ABSENCE REASON |
|---|---|---|
| P0001 | ABSENCE | GENERAL MEDICAL EXAMINATION |
| P0002 | PRESENCE | - |
| ⋮ | | |

FIG. 25

FIRST ESTIMATION BASIS INFORMATION — 95

| ABSENCE REASON | ABSENCE TIME |
|---|---|
| GENERAL MEDICAL EXAMINATION | 30 MINUTES |
| ENDOSCOPIC EXAMINATION | 60 MINUTES |
| MRI EXAMINATION | 60 MINUTES |
| REHABILITATION | 60 MINUTES |
| RESTROOM | 5 MINUTES |
| PURCHASING | 15 MINUTES |
| VISIT | 30 MINUTES |
| BATHING | 30 MINUTES |
| ⋮ | |

```
┌─────────────────────────────────────────────────────┐
│                DELAY CAUSE INPUT SCREEN             │ ~125
├─────────────────────────────────────────────────────┤
```

125

DELAY CAUSE INPUT SCREEN

⚠ PLEASE, ENTER DELAY CAUSE FOR THIS ROUNDING IMAGING IS LATER THAN EXPECTED. — 126

· MAIN CAUSE

FACILITY CONSTRUCTION DEVICE MALFUNCTION
⋮
127

· OCCURRENCE LOCATION

PREPARATION ROOM HALLWAY A2
⋮
128

· OCCURRENCE TIME SLOT

10:00 TO 10:14
10:15 TO 10:29
⋮
129

OK — 130

ROUNDING IMAGING MANAGEMENT APPARATUS, METHOD FOR OPERATING ROUNDING IMAGING MANAGEMENT APPARATUS, PROGRAM FOR OPERATING ROUNDING IMAGING MANAGEMENT APPARATUS, DATA STRUCTURE, AND RECORDING APPARATUS

CROSS-REFERENCE TO RELATED APPLICATIONS

The present application claims priority under 35 U.S.C. § 119 to Japanese Patent Application No., 2019-038837 filed on Mar. 4, 2019. The above application is hereby expressly incorporated by reference, in its entirety, into the present application.

BACKGROUND

1. Technical Invention

A technique of the present disclosure relates to a rounding imaging management apparatus, a method for operating the rounding imaging management apparatus, a program for operating the rounding imaging management apparatus, a data structure, and a recording apparatus.

2. Description of the Related Art

In medical sites, rounding imaging for radiographing individual patients while rounding hospital rooms using a mobile radiography apparatus is performed. JP2018-158026A discloses a technique for creating a rounding route in which a movement distance of a mobile radiography apparatus becomes the shortest on the basis of information on hospital rooms where rounding imaging is to be performed, as a piece of content of a rounding plan of rounding imaging.

SUMMARY

In actual rounding imaging, for example, a necessary time varies depending on various factors such as the presence or absence of an assistant who assists radiography. For this reason, there is a case where a created rounding plan deviates from an actual situation. In a case where such deviation occurs, there is a concern that adverse effects such as delay in other treatments such as inspection or rehabilitation after rounding imaging may occur.

An object of the technique of the present disclosure is to provide a rounding imaging management apparatus capable of performing rounding imaging based on an actual situation, a method for operating the rounding imaging management apparatus, a program for operating the rounding imaging management apparatus, a data structure, and a recording apparatus.

In order to achieve the above object, according to an aspect of the present disclosure, there is provided a rounding imaging management apparatus that manages rounding imaging for radiographing individual patients while rounding hospital rooms using a mobile radiography apparatus, comprising: a first acquisition unit that acquires imaging order information indicating content of the radiography in the rounding imaging to be performed; a second acquisition unit that acquires, from time results data in which a necessary time in the rounding imaging performed in the past is registered, the necessary time; a creation unit that creates a rounding plan of the rounding imaging on the basis of the imaging order information and the necessary time; and an output controller that performs a control for outputting the rounding plan.

It is preferable that the rounding plan includes a rounding route of the mobile radiography apparatus.

It is preferable that an individual necessary time taken for each past radiography is registered as the necessary time in the time results data, the second acquisition unit acquires the individual necessary time corresponding to the radiography indicated by the imaging order information, and the rounding plan includes a predicted total necessary time that is calculated on the basis of the individual necessary time and predicted to be taken for the entire rounding imaging.

It is preferable that the individual necessary time is at least one of an imaging time of the radiography or a movement time of the mobile radiography apparatus, and the time results data is at least one of imaging time results data in which the imaging time is registered or movement time results data in which the movement time is registered.

It is preferable that the time results data is data in which a time slot and the individual necessary time are registered in association with each other, and the individual necessary time varies according to the time slot, and the creation unit creates a shortest time route where the predicted total necessary time becomes the shortest as the rounding route.

It is preferable that the imaging order information includes hospital room information of the hospital room of the patient for whom the rounding imaging is to be performed, and the creation unit creates a shortest distance route where a movement distance of the mobile radiography apparatus becomes the shortest on the basis of the hospital room information, and then, corrects the shortest distance route in accordance with the individual necessary time to create the shortest time route.

It is preferable that the rounding imaging management apparatus further comprises: a third acquisition unit that acquires patient schedule information in which a schedule of treatment for the patient is registered, and the creation unit creates the shortest time route with reference to the patient schedule information.

It is preferable that the rounding imaging management apparatus further comprises: a fourth acquisition unit that acquires assistant schedule information in which a schedule of an assistant who assists the radiography is registered, and the creation unit creates the shortest time route with reference to the assistant schedule information.

It is preferable that the rounding imaging management apparatus further comprises: a fifth acquisition unit that acquires current status information indicating a current status of information that is a source of creation of the rounding plan during the rounding imaging based on the shortest time route; and an updating unit that updates the shortest time route and sets the updated shortest time route in a case where the current status information includes content which changes the individual necessary time, and the output controller outputs the updated shortest time route.

It is preferable that the current status information is at least one of room occupancy status information indicating a room occupancy status in the hospital room of the patient for whom the rounding imaging is to be performed, treatment status information indicating a status of treatment in the hospital room of the patient for whom the rounding imaging is to be performed, availability status information indicating an availability status of an assistant who assists the radiography, or congestion level information indicating a congestion level of a hospital.

It is preferable that the rounding imaging management apparatus further comprises: a first estimation unit that estimates an absence time of the patient indicated as being absent in the room occupancy status information, and the updating unit updates the shortest time route on the basis of the absence time estimated by the first estimation unit.

It is preferable that the rounding imaging management apparatus further comprises: a second estimation unit that estimates, in a case where the treatment status information indicates that the treatment is performed in the hospital room, a treatment time to be taken for the treatment, and the updating unit updates the shortest time route on the basis of the treatment time estimated by the second estimation unit.

It is preferable that the rounding imaging management apparatus comprises: a reception unit that receives, in a case where an actual total necessary time in a case where the rounding imaging is actually performed in accordance with the rounding plan is delayed by a set time or longer from the predicted total necessary time, delay cause information indicating a cause of the delay of the actual total necessary time; and a recording controller that performs a control for recording the delay cause information in a storage unit.

It is preferable that the output controller performs a control for outputting a scheduled start time of the radiography based on the rounding plan.

According to another aspect of the present disclosure, there is provided a method for operating a rounding imaging management apparatus that manages rounding imaging for radiographing individual patients while rounding hospital rooms using a mobile radiography apparatus, comprising: acquiring imaging order information indicating content of the radiography in the rounding imaging to be performed; acquiring, from time results data in which a necessary time in the rounding imaging performed in the past is registered, the necessary time; creating a rounding plan of the rounding imaging on the basis of the imaging order information and the necessary time; and performing a control for outputting the rounding plan.

According to still another aspect of the present disclosure, there is provided a program for operating rounding imaging management apparatus that manages rounding imaging for radiographing individual patients while rounding hospital rooms using a mobile radiography apparatus, that causes a computer to function as: a first acquisition unit that acquires imaging order information indicating content of the radiography in the rounding imaging to be performed; a second acquisition unit that acquires, from time results data in which a necessary time in the rounding imaging performed in the past is registered, the necessary time; a creation unit that creates a rounding plan of the rounding imaging on the basis of the imaging order information and the necessary time; and an output controller that performs a control for outputting the rounding plan.

According to still another aspect of the present disclosure, there is provided a data structure in which a necessary time in rounding imaging performed in the past is registered, in order to manage the rounding imaging for radiographing individual patients while rounding hospital rooms using a mobile radiography apparatus.

According to still another aspect of the present disclosure, there is provided a recording apparatus comprising a recording controller that records a necessary time in rounding imaging performed in the past is stored in a storage unit, in order to manage the rounding imaging for radiographing individual patients while rounding hospital rooms using a mobile radiography apparatus.

According to the technique of the present disclosure, it is possible to provide a rounding imaging management apparatus capable of performing rounding imaging based on an actual situation, a method for operating the rounding imaging management apparatus, a program for operating the rounding imaging management apparatus, a data structure, and a recording apparatus.

BRIEF DESCRIPTION OF THE DRAWINGS

Exemplary embodiments according to the technique of the present disclosure will be described in detail based on the following figures, wherein:

FIG. 15 is a diagram showing imaging time results data according to a second embodiment;

FIG. 16 is a diagram showing movement time results data according to the second embodiment;

FIG. 24 is a diagram showing room occupancy status information;

FIG. 25 is a diagram showing first estimation basis information;

FIG. 39 is a diagram showing a delay cause input screen;

FIG. 43A and FIG. 43B are diagrams showing a scheduled start time display screen, in which FIG. 43A shows a scheduled start time display screen output to a patient's portable terminal, and FIG. 43B shows a scheduled start time display screen output to an assistant's portable terminal.

DETAILED DESCRIPTION

First Embodiment

Figure 1:
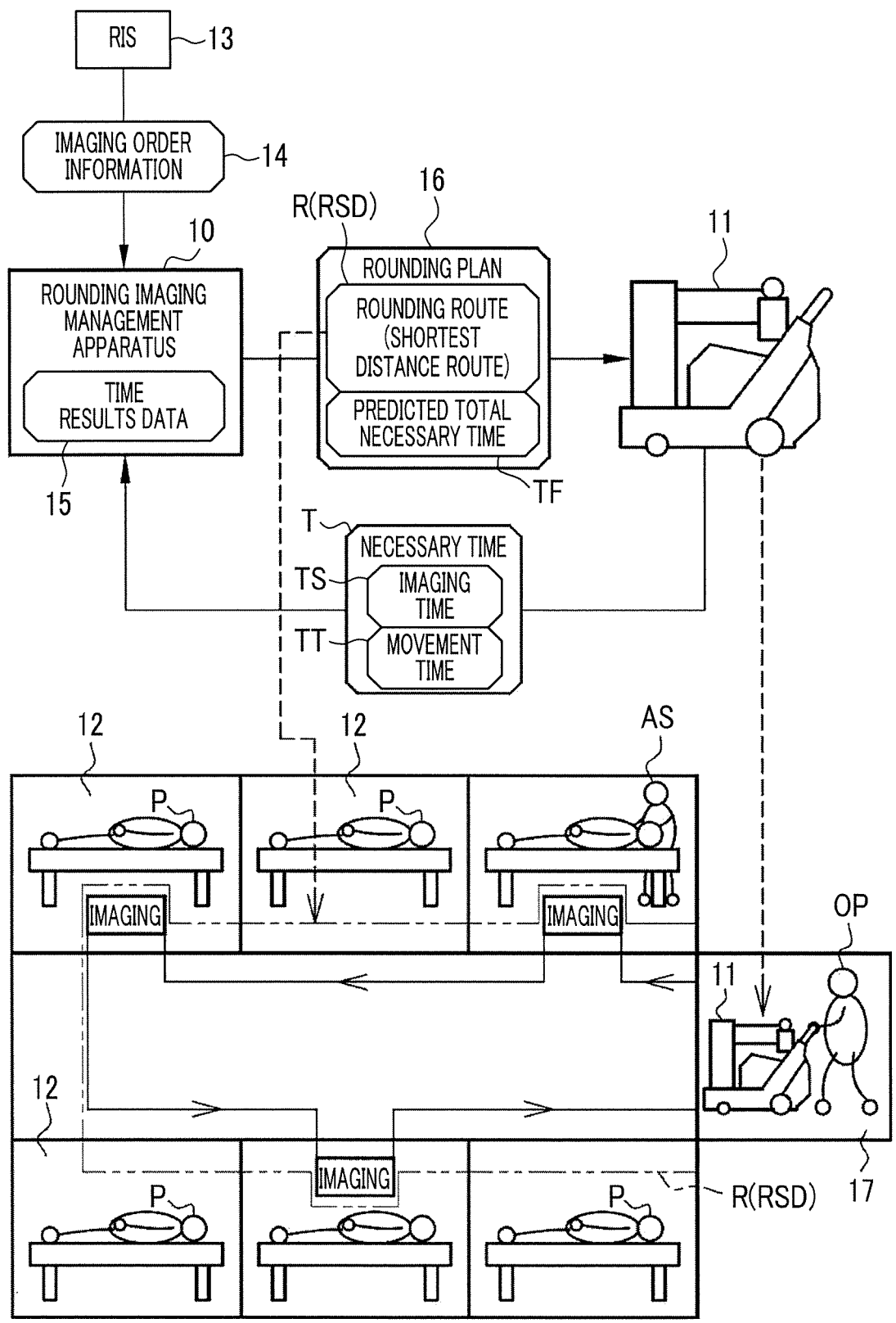
FIG. 1 is a diagram showing a rounding imaging management apparatus.

In FIG. 1, a rounding imaging management apparatus 10 manages rounding imaging for radiographing individual patients P while rounding hospital rooms 12 using a mobile radiography apparatus 11. Hereinafter, for simplicity of description, it is assumed that one patient P is accommodated in one hospital room 12. Further, one mobile radiography apparatus 11 is provided in the figure, but a plurality of mobile radiography apparatuses 11 may be provided.

Imaging order information 14 is transmitted to the rounding imaging management apparatus 10 from a radiology information system (hereinafter, simply referred to as an RIS) 13. The imaging order information 14 is information indicating content of radiography in rounding imaging to be performed (see FIG. 2).

In addition, a necessary time T in rounding imaging performed in the past is transmitted to the rounding imaging management apparatus 10 from the mobile radiography apparatus 11. The necessary time T is, specifically, an imaging time TS of radiography and a movement time TT of the mobile radiography apparatus 11. The necessary time T is registered in time results data 15 (see FIG. 7).

The rounding imaging management apparatus 10 creates a rounding plan 16 of rounding imaging on the basis of the imaging order information 14 and the necessary time T. The rounding imaging management apparatus 10 transmits the created rounding plan 16 to the mobile radiography apparatus 11. An operator OP such as a radiologist who operates the mobile radiography apparatus 11 performs rounding imaging in accordance with the rounding plan 16.

The rounding plan 16 includes a rounding route R of the mobile radiography apparatus 11 and a predicted total necessary time TF predicted to be taken to the entire rounding imaging. The rounding route R is a route in which an operator rounds the hospital rooms 12 of the patients P scheduled for rounding imaging within the shortest distance using a preparation room 17 where the mobile radiography apparatus 11 stands by as a first departure place and a last arrival place. Hereinafter, the rounding route R in which the movement distance of the mobile radiography apparatus 11 is the shortest is expressed as a shortest distance route RSD.

The rounding imaging management apparatus 10 is provided in the preparation room 17, for example. The rounding imaging management apparatus 10, the mobile radiography apparatus 11, and the RIS 13 are connected to each other through a network (not shown) such as an in-hospital wireless local area network (LAN). The rounding imaging management apparatus 10, the mobile radiography apparatus 11, and the RIS 13 transmit and receive various types of information such as the imaging order information 14 or the rounding plan 16 through the network.

Depending on the patients P, in addition to an operator OP, an assistant AS may perform radiography while performing assistance. The assistant AS is, for example, a radiologist or a nurse other than the operator OP. As an example in which assistance of the assistant AS is recommended, there is a case where a medical condition of a patient P is serious and the patient P cannot move by his or her own intention.

Figures 2, 3:
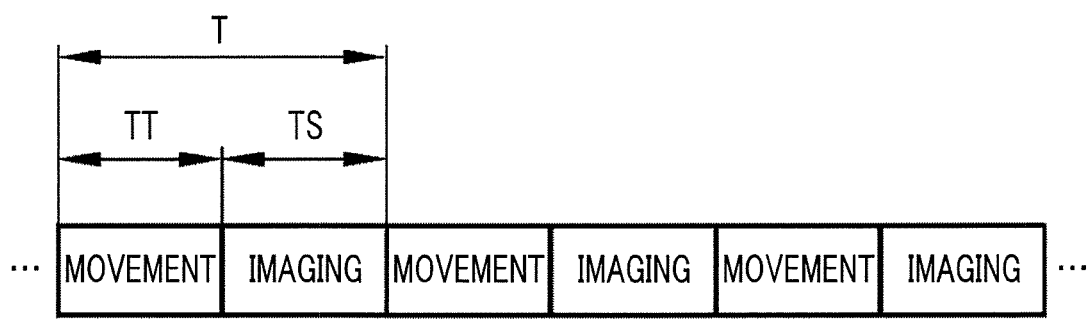
FIG. 2 is a diagram showing imaging order information.
FIG. 3 is a diagram showing an imaging time, a movement time, and a necessary time.

As shown in FIG. 2, content of radiography in rounding imaging to be performed is registered for each order ID (identification data) for identifying individual imaging orders, in the imaging order information 14. More specifically, the imaging order information 14 includes items such as a patient ID for identifying each patient P, a name of the patient P, hospital room information 20 of the hospital room 12 of the patient P, and an imaging technique.

The hospital room information 20 is specifically a number of the hospital room 12. The imaging technique includes an imaging type such as "simple imaging", an imaging area such as a "chest front lying position", an imaging direction, and a posture. The imaging type includes "simple imaging", "videofluoroscopy", "energy subtraction imaging", "tomosynthesis imaging", and the like. The imaging area includes "chest", "head", "abdomen", "waist", "thigh", and the like. The imaging direction includes "front", "back", "side", and the like. The posture includes "lying position", "side lying position", "sitting posture", and the like. In addition to the above exemplified items, items such as an age of a patient P, a gender, a height, a weight, a disease name, a medical condition, or a physician ID of a doctor who issued an imaging order may be added.

As shown in FIG. 3, movement between hospital rooms and radiography are repeated in the rounding imaging. The imaging time TS refers to a period time from a time when movement to a certain hospital room 12 is completed to a time when radiography in the hospital room 12 is completed and movement to the next hospital room 12 is started. The movement time TT is a period of time from a time when the radiography in the hospital room 12 is completed and the movement to the next hospital room 12 is started to a time when the movement to the next hospital room 12 is completed. Further, a time obtained by adding up the imaging time TS and the movement time TT is the necessary time T. That is, the necessary time T is an individually necessary time taken to each of the past radiography.

A clocking start timing and a clocking end timing of the imaging time TS and a clocking start timing and a clocking end timing of the movement time TT are input to the mobile radiography apparatus 11 by the operator OP. For example, an operation of a lock mechanism of which rotational lock is connected to wheels of the mobile radiography apparatus 11 is set as the clocking start timing of the imaging time TS and the clocking end timing of the movement time TT, and release of the lock mechanism is set as the clocking end timing of the imaging time TS and the clocking start timing of the movement time TT. Using a global positioning system (GPS) or a wireless beacon signal, position information of the mobile radiography apparatus 11 in a hospital may be acquired in time series, and a stay time of the mobile radiography apparatus 11 in each hospital room 12 may be set as the imaging time TS and a time between the respective imaging times TS may be set as the movement time TT.

Figure 4:
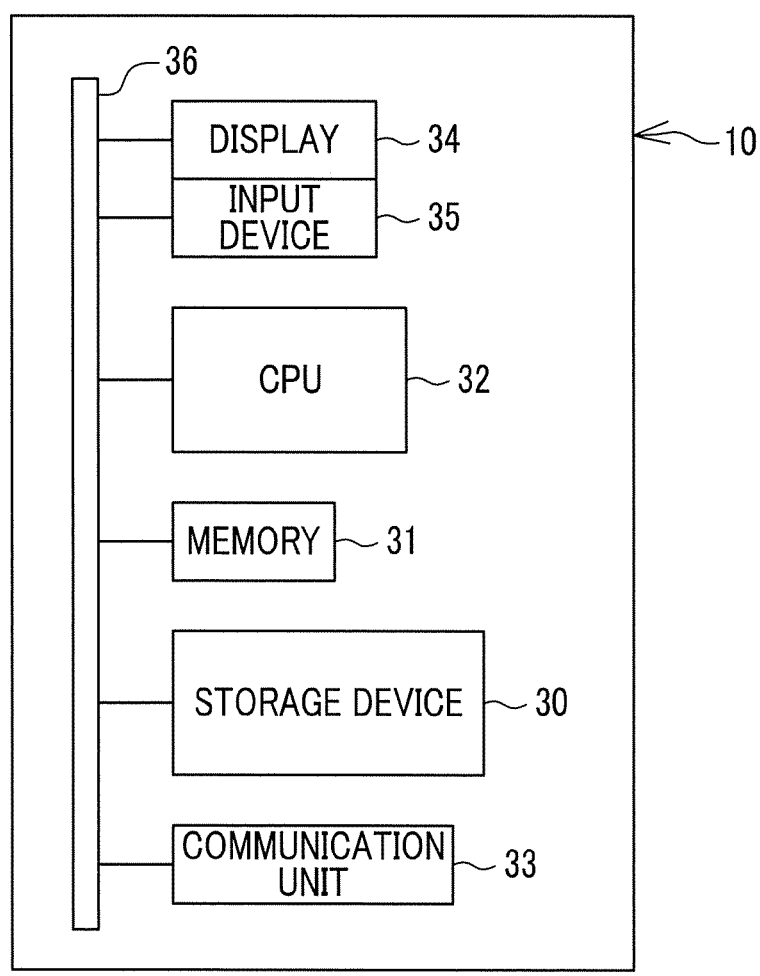
FIG. 4 is a block diagram showing a computer that configures the rounding imaging management apparatus.

In FIG. 4, a computer that configures the rounding imaging management apparatus 10 comprises a storage device 30, a memory 31, a central processing unit (CPU) 32, a communication unit 33, a display 34, and an input device 35. These are connected to each other through a busline 36.

The storage device 30 is a hard disk drive that is provided in the computer that configures the rounding imaging management apparatus 10 or is connected to the computer through a cable or a network. Alternatively, the storage device 30 is a disk array in which a plurality of hard disk drives are connected in series. The storage device 30 stores a control program for an operating system or the like, a variety of application programs, a variety of data associated with these programs, and the like.

The memory 31 is a work memory for the CPU 32 to execute processing. The CPU 32 loads the programs stored in the storage device 30 into the memory 31, and executes processing in accordance with the program to generally control respective units of the computer.

The communication unit 33 is a network interface that controls transmission of a variety of information through a network. The display 34 displays a variety of screens. The computer that configures the rounding imaging management apparatus 10 receives an input of an operating instruction from the input device 35 through the variety of screens. The input device 35 is a keyboard, a mouse, a touch panel, or the like.

Figure 5:
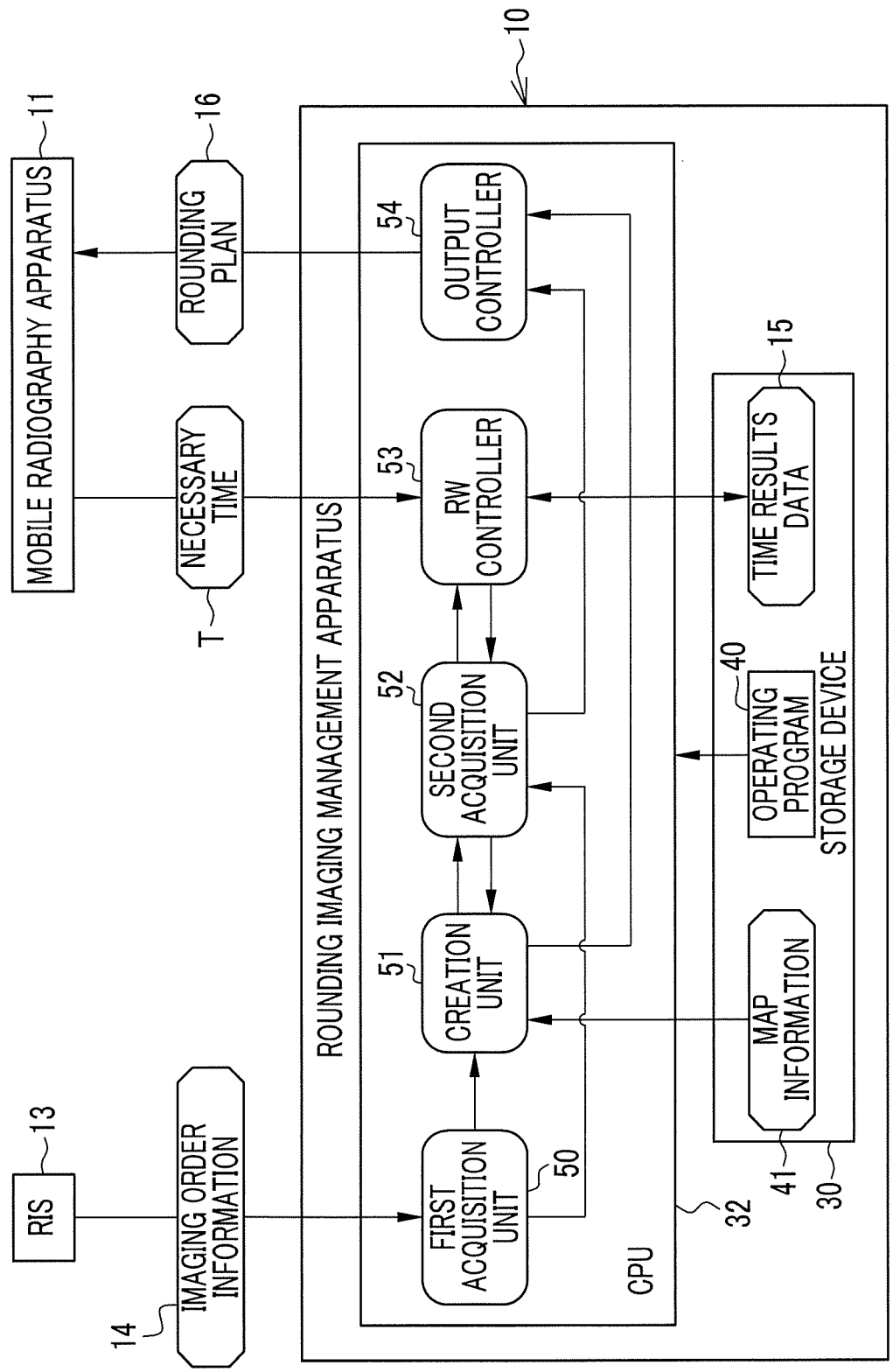
FIG. 5 is a block diagram of a CPU of the rounding imaging management apparatus.

In FIG. 5, an operating program 40 is stored in the storage device 30 of the rounding imaging management apparatus 10 as an application program. The operating program 40 is an application program for causing a computer to function as the rounding imaging management apparatus 10. The operating program 40 is an example of an "operating program of the rounding imaging management apparatus" according to the technique of the present disclosure. Map information 41 and time results data 15, in addition to the operating program 40, are stored in the storage device 30.

In a case where the operating program 40 is activated, the CPU 32 of the rounding imaging management apparatus 10 cooperates with the memory 31 or the like to function as a first acquisition unit 50, a creation unit 51, a second acquisition unit 52, a read/write (hereinafter referred to as RW) controller 53, and an output controller 54.

The first acquisition unit 50 acquires imaging order information 14 from the RIS 13. The first acquisition unit 50 outputs the acquired imaging order information 14 to the creation unit 51 and the second acquisition unit 52.

The creation unit 51 creates the rounding plan 16 including a rounding route R (shortest distance route RSD) and a predicted total necessary time TF. The creation unit 51 outputs the created rounding plan 16 to the second acquisition unit 52 and the output controller 54.

The second acquisition unit 52 acquires a necessary time T from the time results data 15. The second acquisition unit 52 outputs the acquired necessary time T to the creation unit 51 and the output controller 54.

The RW controller 53 records the necessary time T from the mobile radiography apparatus 11 in the storage device 30. That is, the RW controller 53 is an example of a "recording controller" according to the technique of the present disclosure. Further, the storage device 30 is an example of a "storage unit" according to the technique of the present disclosure. Further, the rounding imaging management apparatus 10 is an example of a "recording apparatus" according to the technique of the present disclosure.

The RW controller 53 reads out the necessary time T from the time results data 15. More specifically, the RW controller 53 reads out the imaging time TS corresponding to radiography indicated by the imaging order information 14 in accordance with a request from the second acquisition unit 52. Further, in accordance with the request from the second acquisition unit 52, the RW controller 53 reads out the movement time TT corresponding to each route between rooms of the shortest distance route RSD. The RW controller 53 outputs the read-out imaging time TS and movement time TT to the second acquisition unit 52. The output controller 54 performs a control for outputting the rounding plan 16 to the mobile radiography apparatus 11.

Figure 6:
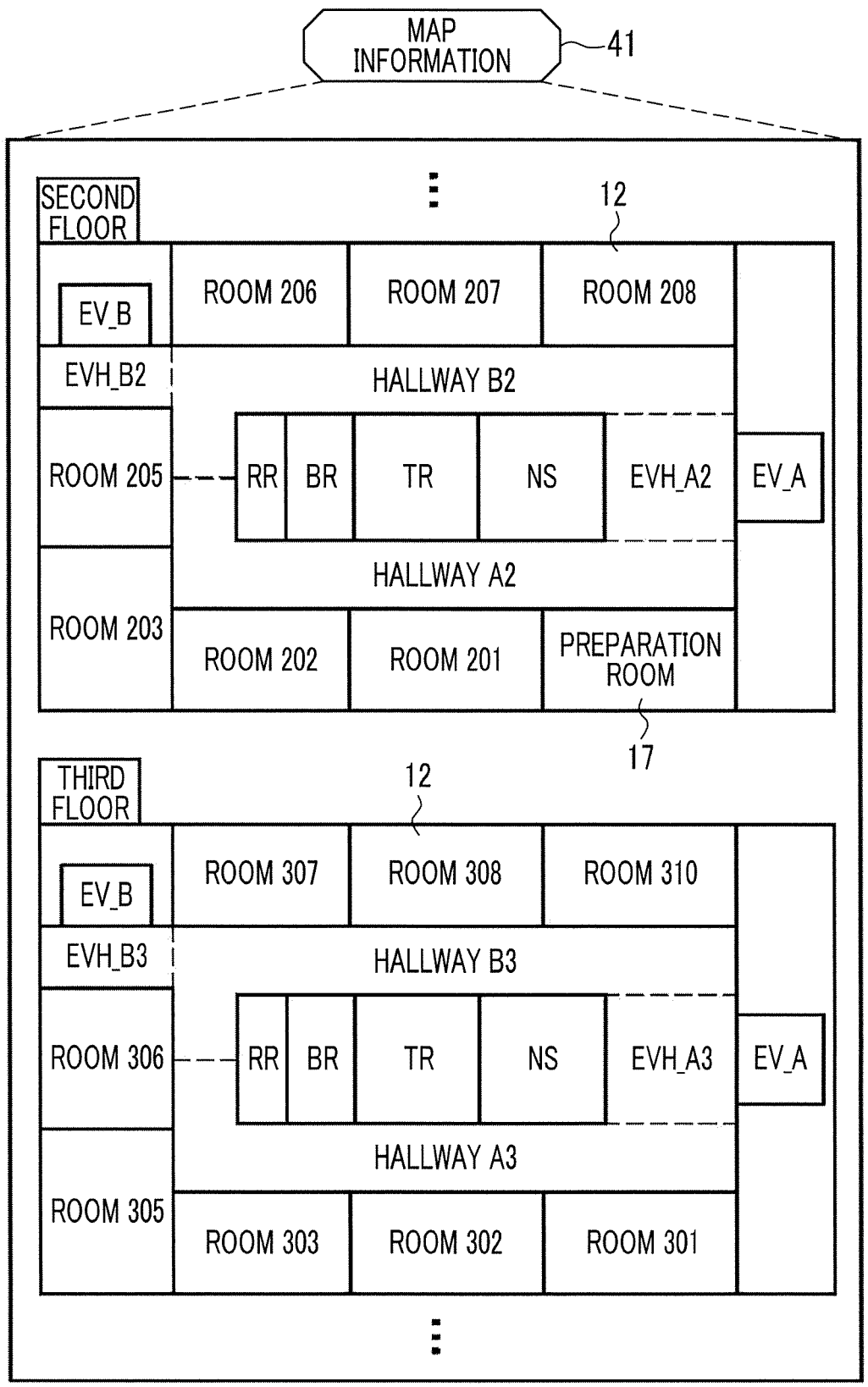
FIG. 6 is a diagram showing map information.

In FIG. 6, the map information 41 is information indicating arrangement of the hospital rooms 12 and the like on floors in the hospital to which the mobile radiography apparatus 11 is moved. FIG. 6 shows the map information 41 on the second and third floors as an example.

On the second floor, there are seven hospital rooms 12 such as a room 201 or a room 202, and a preparation room 17. On the third floor, there are eight hospital rooms 12 such as a room 301 or a room 302. Further, a nurse station (indicated as NS in the figure), a treatment room (indicated as TR in the figure), a bathroom (indicated as BR in the figure), and a toilet (indicated as RR in the figure) are commonly provided on the second and third floors.

Further, on the second floor, there are a hallway A2, a hallway B2, an elevator hall (indicated as EVH in the figure) A2, and an elevator hall B2. Similarly, on the third floor, there are a hallway A3, a hallway B3, an elevator hall A3, and an elevator hall B3. The elevator hall A2 and the elevator hall A3 are halls for an elevator (indicated as EV in the figure) A. The elevator hall B2 and the elevator hall B3 are halls for an elevator B.

Figure 7:
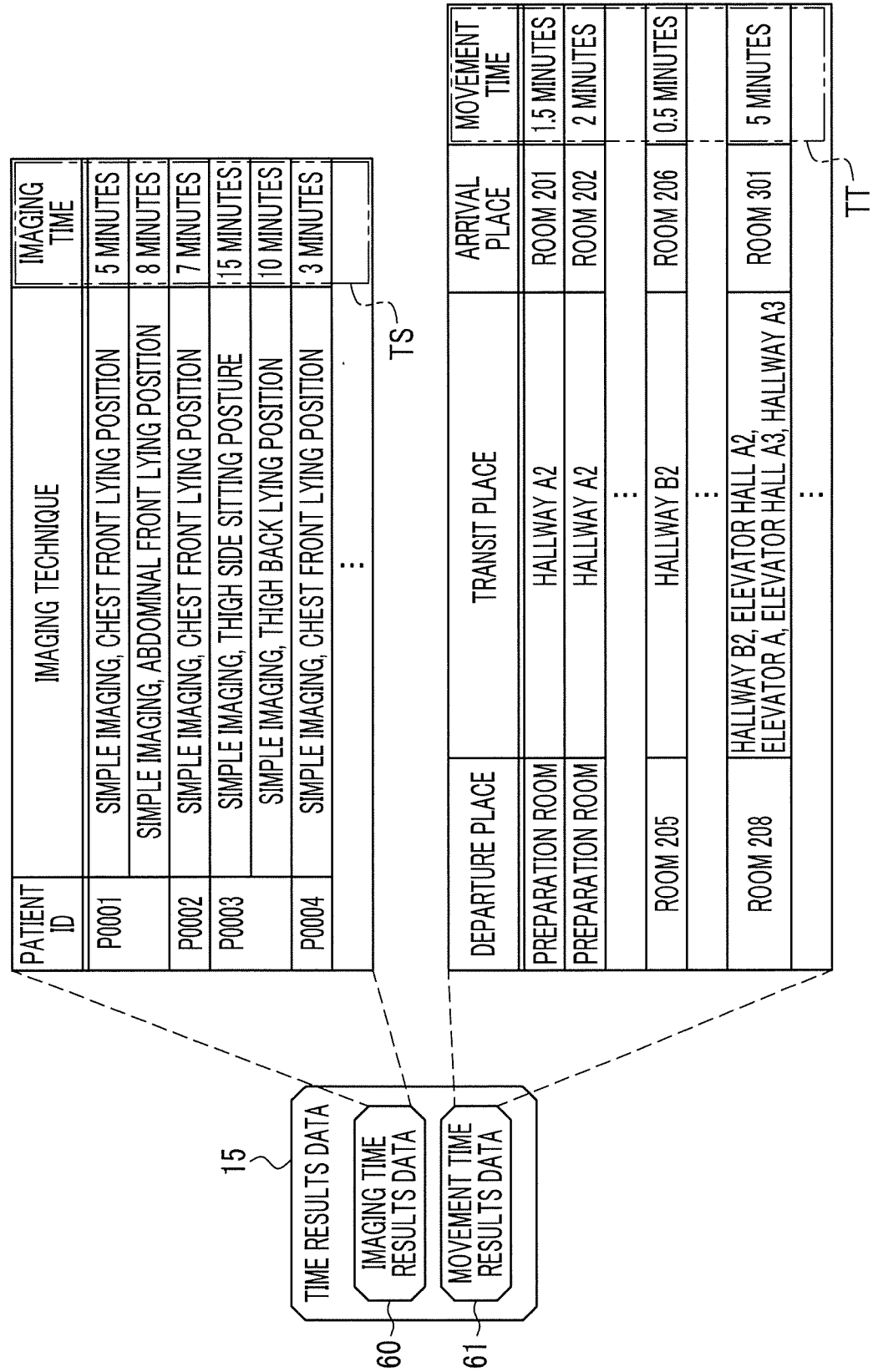
FIG. 7 is a diagram showing time results data.

In FIG. 7, the time results data 15 includes imaging time results data 60 and movement time results data 61. The imaging time results data 60 is data in which the imaging time TS is registered for each patient ID and each imaging technique. The movement time results data 61 is data in which the movement time TT is registered for each route between a departure place, a transit place, and an arrival place of the mobile radiography apparatus 11. In this way, the time results data 15 is an example of a "data structure" according to the technique of the present disclosure.

In a case where the same patient P is radiographed a plurality of times with the same imaging technique, the imaging time TS registered in the imaging time results data 60 is a representative value of respective imaging times TS of the plurality of times of radiography. The representative value is at least one of, for example, an average value, a median value, a mode value, a maximum value, or a minimum value. Similarly, in a case where the mobile radiography apparatus 11 has moved the same departure place, transit place, and arrival place a plurality of times, the movement time TT registered in the movement time results data 61 is a representative value of respective movement times TT of the plurality of movements.

The plurality of imaging times TS used for deriving the representative value may be limited to respective imaging times TS of a plurality of times of radiography performed within the last one week, for example, and the imaging time TS of radiography performed before the last one week may be sequentially deleted from the imaging time results data 60. Similarly, with respect to the movement time TT, a plurality of movement times TT used for deriving the representative value may be limited to respective movement times TT of a plurality of movements within the last one week, and the movement time TT of movement before the last one week may be sequentially deleted from the movement time results data 61.

In FIG. 7, imaging time results data 60 in which the imaging time TS of a patient ID "P0001" and a imaging technique "simple imaging and chest front lying position" is registered to "5 minutes", and the imaging time TS of a patient ID "P0003" and an imaging technique "simple imaging and thigh side sitting posture" is registered to "15 minutes", and the like, is shown as an example. Further, in FIG. 7, the movement time results data 61 in which the movement time TT of a departure place "preparation room", a transit place "hallway A2", and an arrival place "room 201" is registered to "1.5 minutes", and the movement time TT of a departure place "room 208", a transit place "hallway B2, elevator hall A2, elevator A, elevator A3, and hallway A3", and an arrival place "room 301" is registered to "5 minutes", and the like, is shown as an example.

Figure 8:
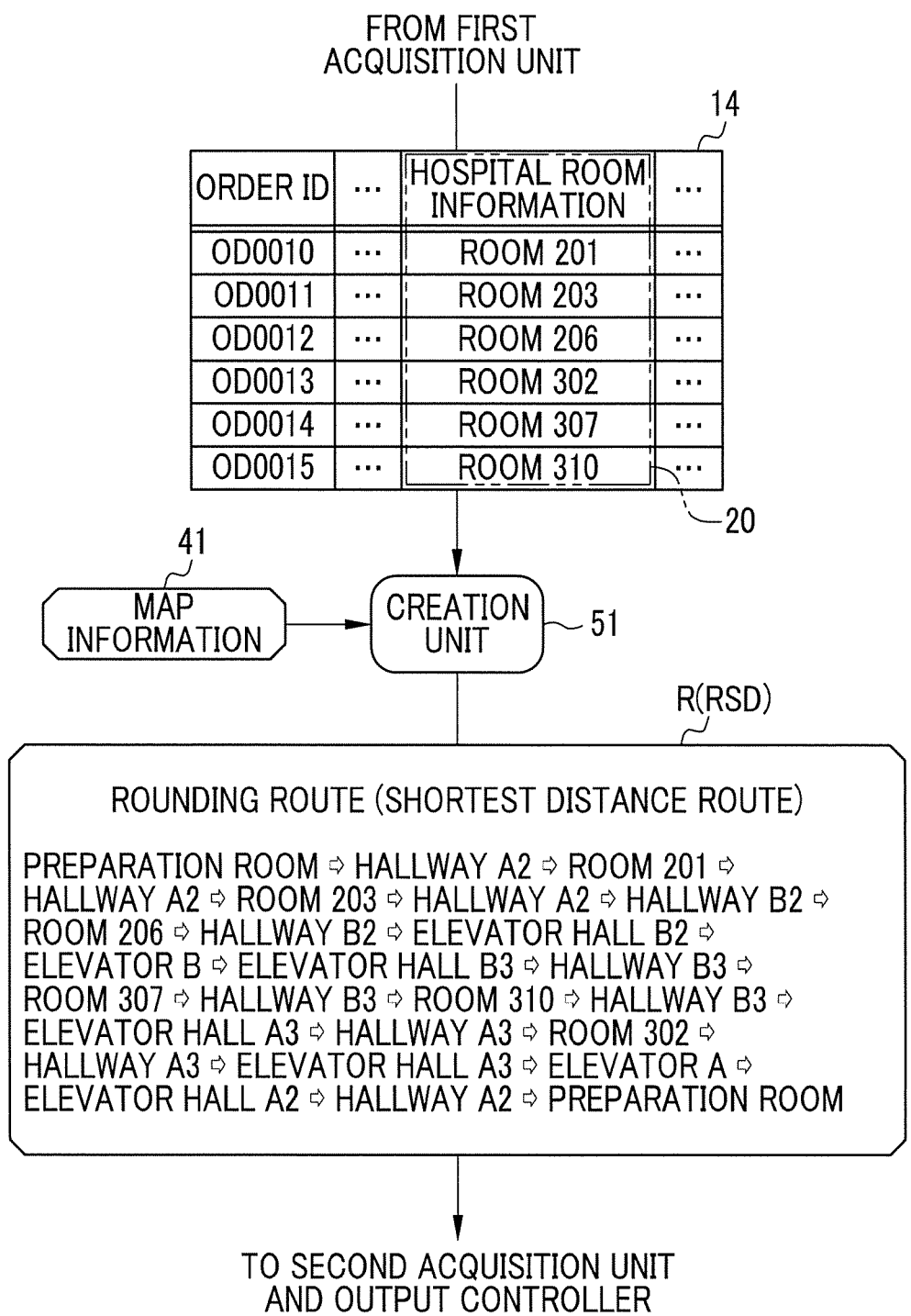
FIG. 8 is a diagram showing a state where a rounding route is created in a creation unit.

In FIG. 8, the creation unit 51 creates the shortest distance route RSD, on the basis of the map information 41, and the hospital room information 20 of the imaging order information 14 from the first acquisition unit 50. The creation unit 51 outputs the created shortest distance route RSD to the second acquisition unit 52 and the output controller 54.

In FIG. 8, there are cases where six imaging orders registered in the imaging order information 14 are correspond to order IDs "OD0010" to "OD0015", and the hospital room information 20 of each imaging order corresponds to the "room 201", a "room 203", a "room 206", the "room 302", a "room 307", and a "room 310". In this case, the creation unit 51 creates the following shortest distance route RSD shown in FIG. 9. That is, an operator arrives at the room 201 from the preparation room 17 through the hallway A2 and performs radiography in the room 201, and then, arrives at the room 203 from the room 201 through the hallway A2 and performs radiography in the room 203. Further, the operator arrives at the room 206 from the room 203 through the hallway A2 and the hallway B2, and performs radiography in the room 206. Then, the operator arrives at the room 307 from the room 206 through the hallway B2, the elevator hall B2, the elevator B, the elevator hall B3, and the hallway B3 and, and performs radiography in the room 307. Further, the operator arrives at the room 310 from the room 307 through the hallway B3 and performs radiography in the room 310, and then, arrives at the room 302 from the room 310 through the hallway B3, the elevator hall A3, and the hallway A3 and performs radiography in the room 302. Finally, the operator returns to the preparation room 17 from the room 302 through the hallway A3, the elevator hall A3, the elevator A, the elevator hall A2, and the hallway A2.

Figure 10:
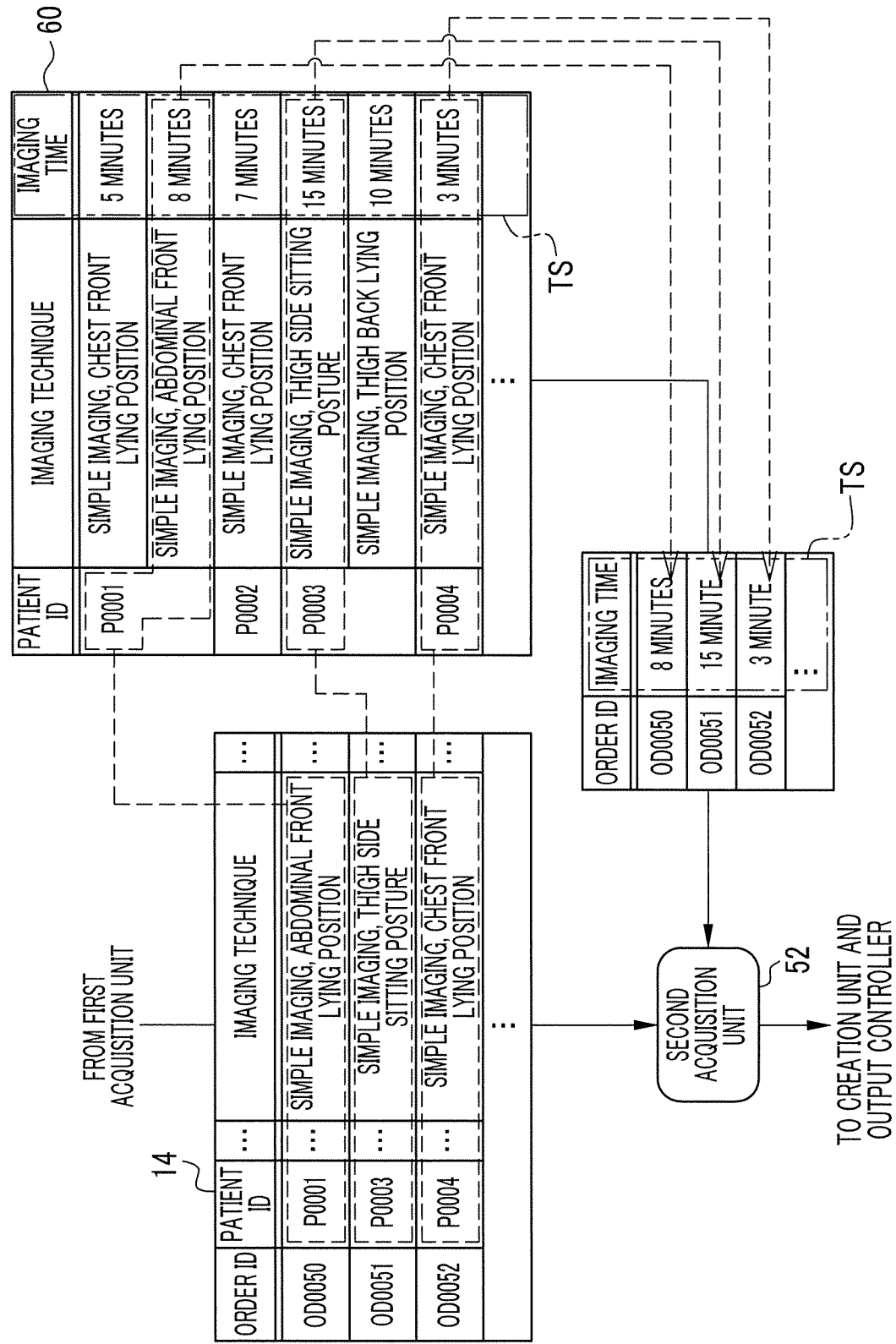
FIG. 10 is a diagram showing a state where an imaging time is acquired in a second acquisition unit.

As shown in FIG. 10, the second acquisition unit 52 acquires the imaging time TS corresponding to the radiography indicated by the imaging order information 14 from the first acquisition unit 50, from the imaging time results data 60. The second acquisition unit 52 outputs the acquired imaging time TS to the creation unit 51 and the output controller 54.

FIG. 10 shows a case where imaging orders such as a patient ID "P0001" and an imaging technique "simple imaging and abdominal front lying position", a patient ID "P0003" and an imaging technique "simple imaging and thigh side sitting posture", and a patient ID "P0004" and an imaging technique "simple imaging and chest front lying position" are registered in the imaging order information 14. In this case, the second acquisition unit 52 acquires, from the imaging time results data 60, the imaging time TS "8 minutes" of the patient ID "P0001" and the imaging technique "simple imaging and abdominal front lying position", the imaging time TS "15 minutes" of the patient ID "P0003" and the imaging technique "simple imaging and thigh side sitting posture", the imaging time TS "3 minutes" of the patient ID "P0004" and the imaging technique "simple imaging and chest front lying position", and the like.

Figure 11:
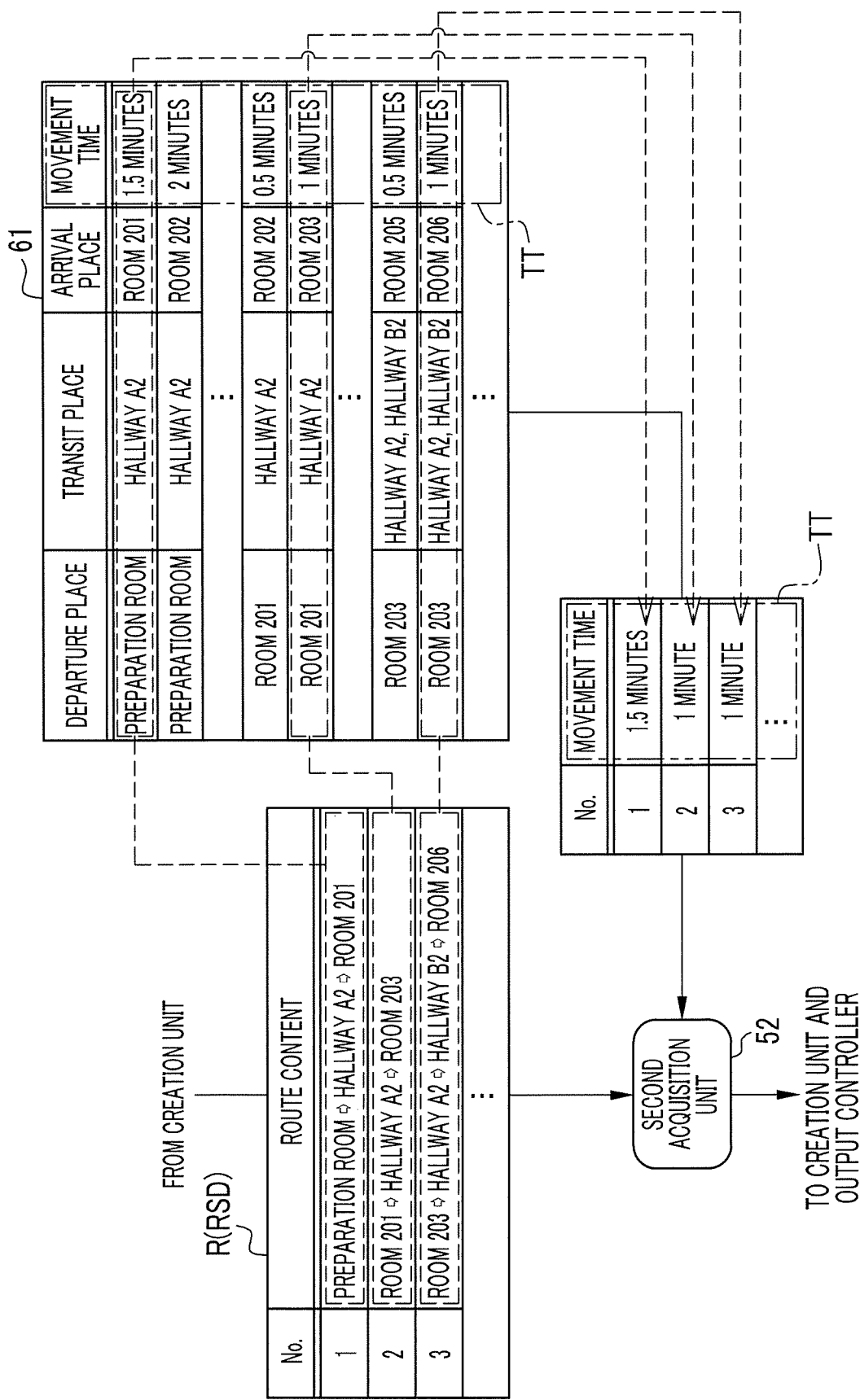
FIG. 11 is a diagram showing a state where a movement time is acquired in the second acquisition unit.

Further, as shown in FIG. 11, the second acquisition unit 52 acquires the movement times TT corresponding to respective routes between rooms of the shortest distance route RSD from the creation unit 51, from the movement time results data 61. The second acquisition unit 52 outputs the acquired movement times TT to the creation unit 51 and the output controller 54.

In FIG. 11, a route 1 where an operator arrives at the room 201 from the preparation room 17 through the hallway A2, a route 2 where the operator arrives at the room 203 from the room 201 through the hallway A2, a route 3 where the operator arrives at the room 206 from the room 203 through the hallway A2 and the hallway B2, and the like, are shown as the shortest distance route RSD. In this case, the second acquisition unit 52 acquires "1.5 minutes" that corresponds to the movement time TT of a departure place "preparation room", a transit place "hallway A2", and an arrival place "room 201", "1 minutes" that corresponds to the movement time TT of a departure place "room 201", a transit place "hallway A2", and an arrival place "room 203", "1 minutes" that corresponds to the movement time TT of a departure place "room 203", a transit place "hallway A2 and hallway B2", and an arrival place "room 206", "1 minute", and the like, from the movement time results data 61, respectively.

Figure 12:
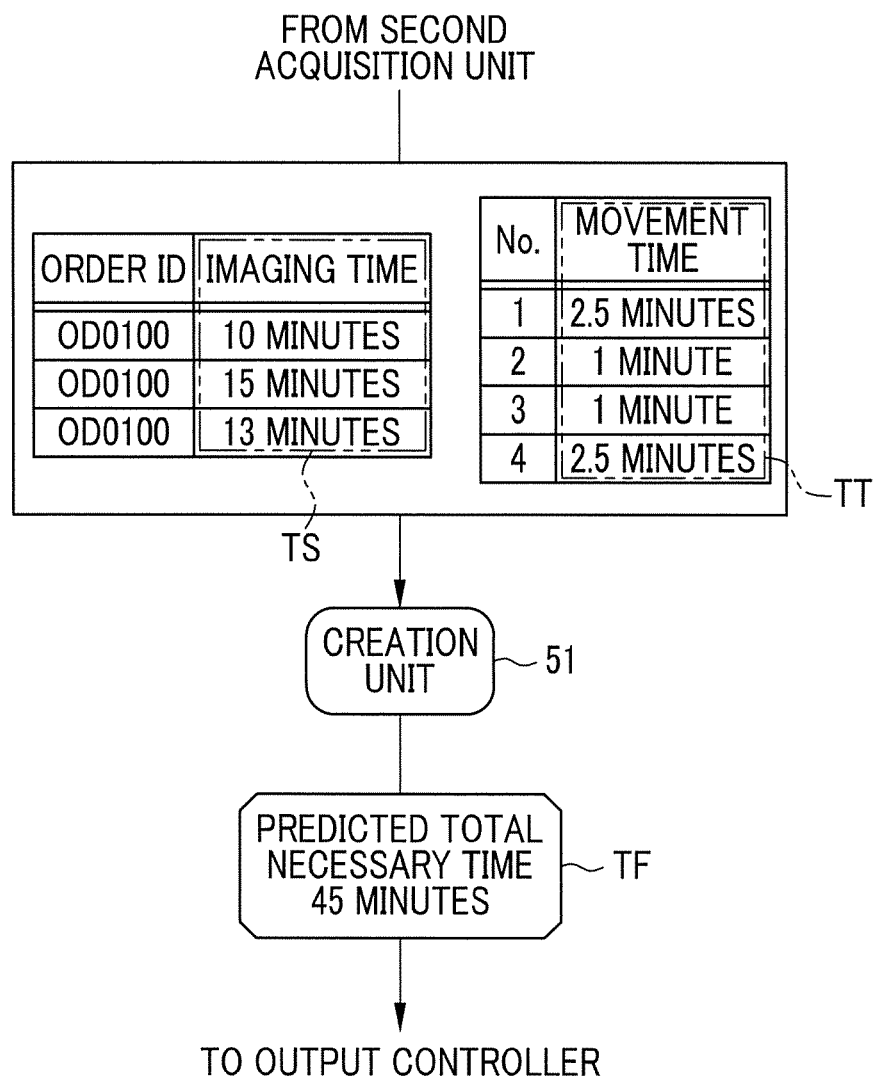
FIG. 12 is a diagram showing a state where a predicted total necessary time is calculated in a creation unit.

As shown in FIG. 12, the creation unit 51 calculates a total of the imaging time TS and the movement time TT from the second acquisition unit 52 as a predicted total necessary time TF. The creation unit 51 outputs the calculated predicted total necessary time TF to the output controller 54.

In FIG. 12, a case where "10 minutes", "15 minutes", and "13 minutes" are acquired as the imaging times TS and "2.5 minutes", "1 minute", "1 minute", and "2.5 minutes" are acquired as the movement times TT is shown. In this case, the predicted total necessary time TF becomes 45 minutes (=10+15+13+2.5+1+1+2.5).

Figure 13:
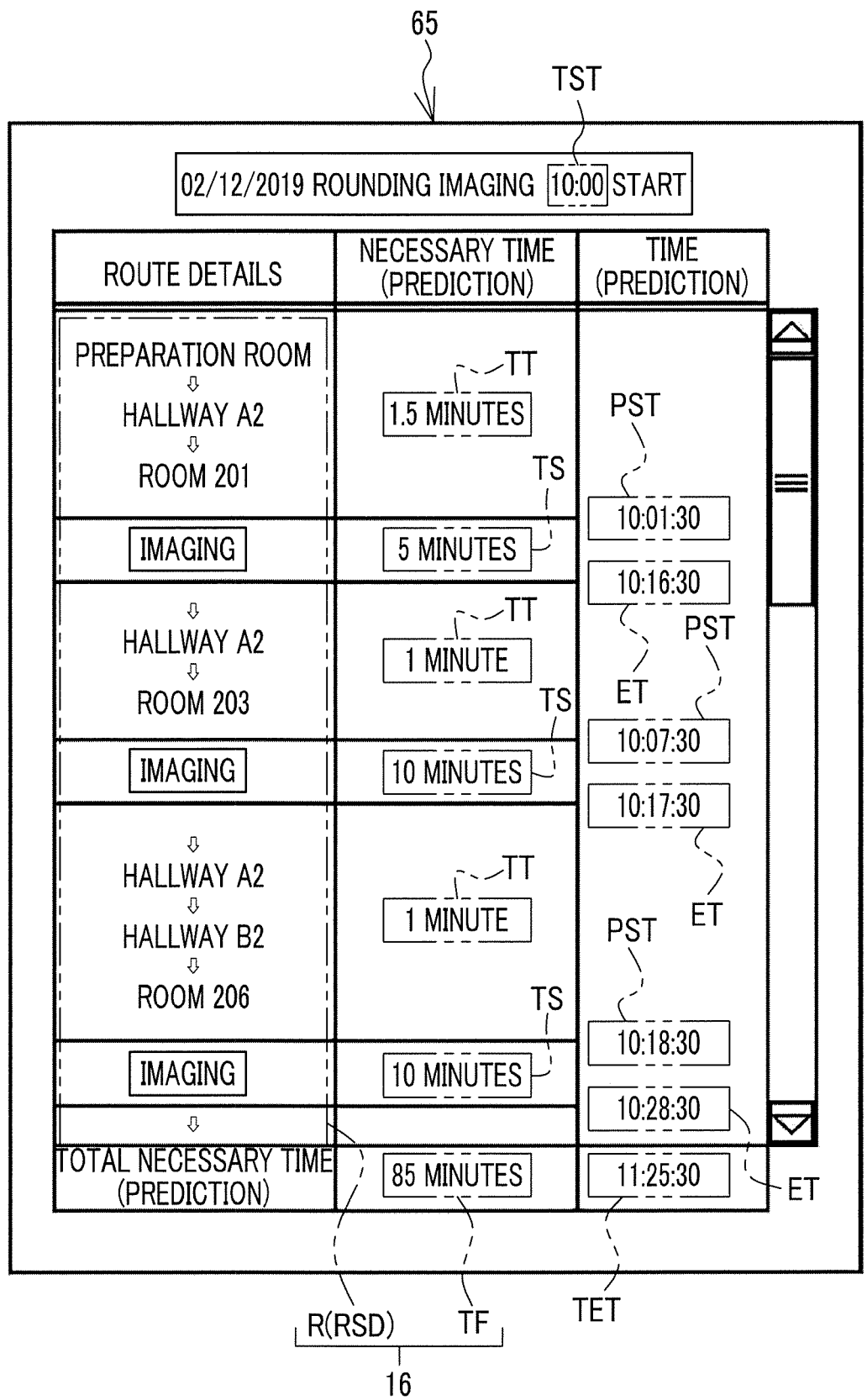
FIG. 13 is a diagram showing a rounding plan display screen.

As shown in FIG. 13, the output controller 54 outputs the rounding plan 16 in the form of the rounding plan display screen 65. The mobile radiography apparatus 11 displays the rounding plan display screen 65 on a display (not shown), and provides the rounding plan 16 for browsing of the operator OP.

The rounding route R (shortest distance route RSD) and the predicted total necessary time TF from the creation unit 51, that is, the rounding plan 16, and the imaging time TS and the movement time TT from the second acquisition unit 52 are displayed on the rounding plan display screen 65. Further, a scheduled start time PST and a scheduled end time ET of each radiography, and a scheduled end time TET of entire rounding imaging are displayed on the rounding plan display screen 65. The scheduled start time PST and the scheduled end time ET of each radiography, and the scheduled end time TET of the entire rounding imaging may be obtained from the scheduled start time TST, the imaging time TS, and the movement time TT of the entire rounding imaging.

Figure 14:
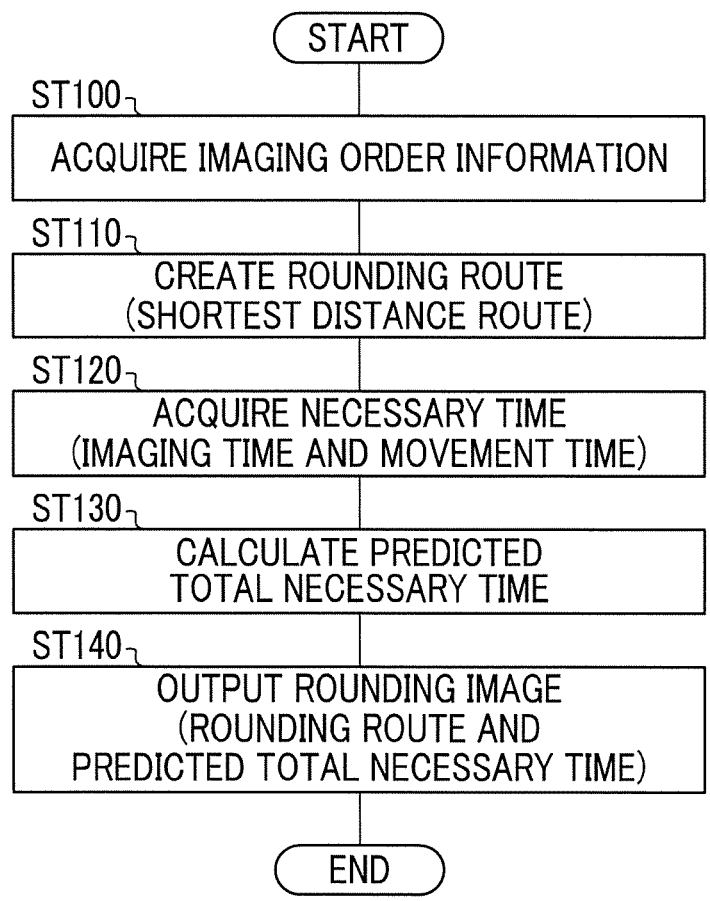
FIG. 14 is a flowchart showing a processing procedure of the rounding imaging management apparatus.

Next, an operation of the above-described configuration will be described with reference to a flowchart shown in FIG. 14. First, in a case where the operating program 40 is activated, as shown in FIG. 5, the CPU 32 of the rounding imaging management apparatus 10 functions as the first acquisition unit 50, the creation unit 51, the second acquisition unit 52, the RW controller 53, and the output controller 54.

The imaging order information 14 is transmitted from the RIS 13 to the rounding imaging management apparatus 10. The imaging order information 14 is acquired by the first acquisition unit 50 (step ST100). The imaging order information 14 is output to the creation unit 51 and the second acquisition unit 52 from the first acquisition unit 50. Step ST100 is an example of "a first acquisition step" according to the technique of the present disclosure.

Figure 9:
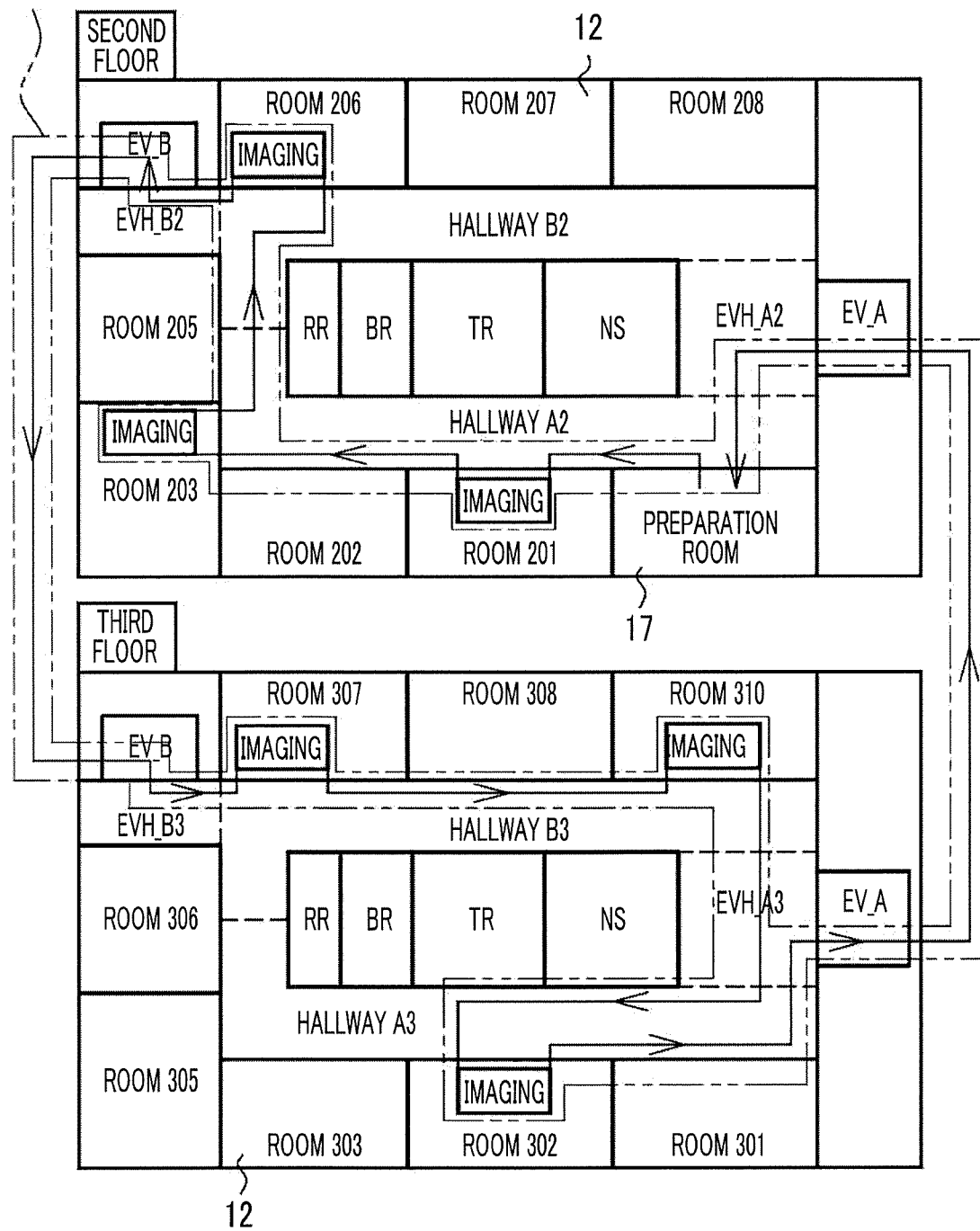
FIG. 9 is a diagram showing the rounding route shown in FIG. 8 with map information.

As shown in FIGS. 8 and 9, the shortest distance route RSD is created by the creation unit 51 (step ST110). The shortest distance route RSD is output to the second acquisition unit 52 and the output controller 54 from the creation unit 51. Step ST110 is an example of "a creation step" according to the technique of the present disclosure.

As shown in FIGS. 10 and 11, the imaging time TS is acquired from the imaging time results data 60, and the movement time TT is acquired from the movement time results data 61, respectively, in the second acquisition unit 52 (step ST120). The imaging time TS and the movement time TT are output to the creation unit 51 from the second acquisition unit 52. Step ST120 is an example of "a second acquisition step" according to the technique of the present disclosure.

As shown in FIG. 12, the predicted total necessary time TF is calculated on the basis of the imaging time TS and the movement time TT by the creation unit 51 (step ST130). The predicted total necessary time TF is output to the output controller 54 from the creation unit 51. Step ST130 is an example of "a creation step" according to the technique of the present disclosure, similar to step ST110.

In the output controller 54, on the basis of the shortest distance route RSD and the predicted total necessary time TF from the creation unit 51, and the imaging time TS and the movement time TT from the second acquisition unit 52, the rounding plan display screen 65 shown in FIG. 13 is generated. The rounding plan display screen 65 is output to the mobile radiography apparatus 11 under the control of the output controller 54 (step ST140). Step ST140 is an example of "an output control step" according to the technique of the present disclosure.

The rounding plan display screen 65 is displayed on a display of the mobile radiography apparatus 11, and is provided for browsing of the operator OP. In accordance with the rounding plan 16 displayed on the rounding plan display screen 65, the operator OP performs rounding imaging.

The necessary time T is transmitted from the mobile radiography apparatus 11 to the rounding imaging management apparatus 10. The necessary time T is registered in the time results data 15 of the storage device 30 by the RW controller 53.

As described above, the rounding imaging management apparatus 10 comprises the first acquisition unit 50 that acquires the imaging order information 14 representing content of radiography in rounding imaging to be performed, the second acquisition unit 52 that acquires the necessary time T in the past rounding imaging, the creation unit 51 that creates the rounding plan 16 on the basis of the imaging order information 14 and the necessary time T, and the output controller 54 that controls an output of the rounding plan 16. Thus, it is possible to perform rounding imaging based on an actual situation, compared with a case where the rounding plan 16 is created on the basis of a virtual necessary time instead of the necessary time T in the past rounding imaging.

As shown in FIG. 12, the creation unit 51 calculates the predicted total necessary time TF. Since the predicted total necessary time TF is calculated on the basis of the imaging time TS and the movement time TT, the accuracy is relatively high. For this reason, the predicted total necessary time TF is considered to have a small difference from an actual total necessary time, which is a total necessary time in a case where the rounding imaging is actually performed in accordance with the rounding plan 16. Accordingly, it is possible to easily schedule other treatments such as inspection or rehabilitation after rounding imaging.

As shown in FIG. 7, the necessary time T is the imaging time TS and the movement time TT, and the time results data 15 is the imaging time results data 60 and the movement time results data 61. Accordingly, it is possible to create a more detailed rounding plan 16.

An individual necessary time may be at least one of the imaging time TS or the movement time TT. Further, the time results data 15 may be at least one of the imaging time results data 60 or the movement time results data 61.

In a case where an imaging order is added during rounding imaging, the creation unit 51 recreates the rounding plan 16 that takes into account the added imaging order.

The individual necessary time such as the imaging time TS and the movement time TT may vary depending on a skill level of the operator OP. For this reason, it is preferable to provide an item of the operator ID of the operator OP in the time results data 15. Then, it is possible to create the rounding plan 16 according to the skill level of each operator OP.

A plurality of patients P may be accommodated in one hospital room 12. In this case, a movement time between beds of each patient P in the same hospital room 12 may also be registered in the movement time results data 61, and the rounding plan 16 may be created in consideration of the movement time between the beds.

Second Embodiment

Figure 17:
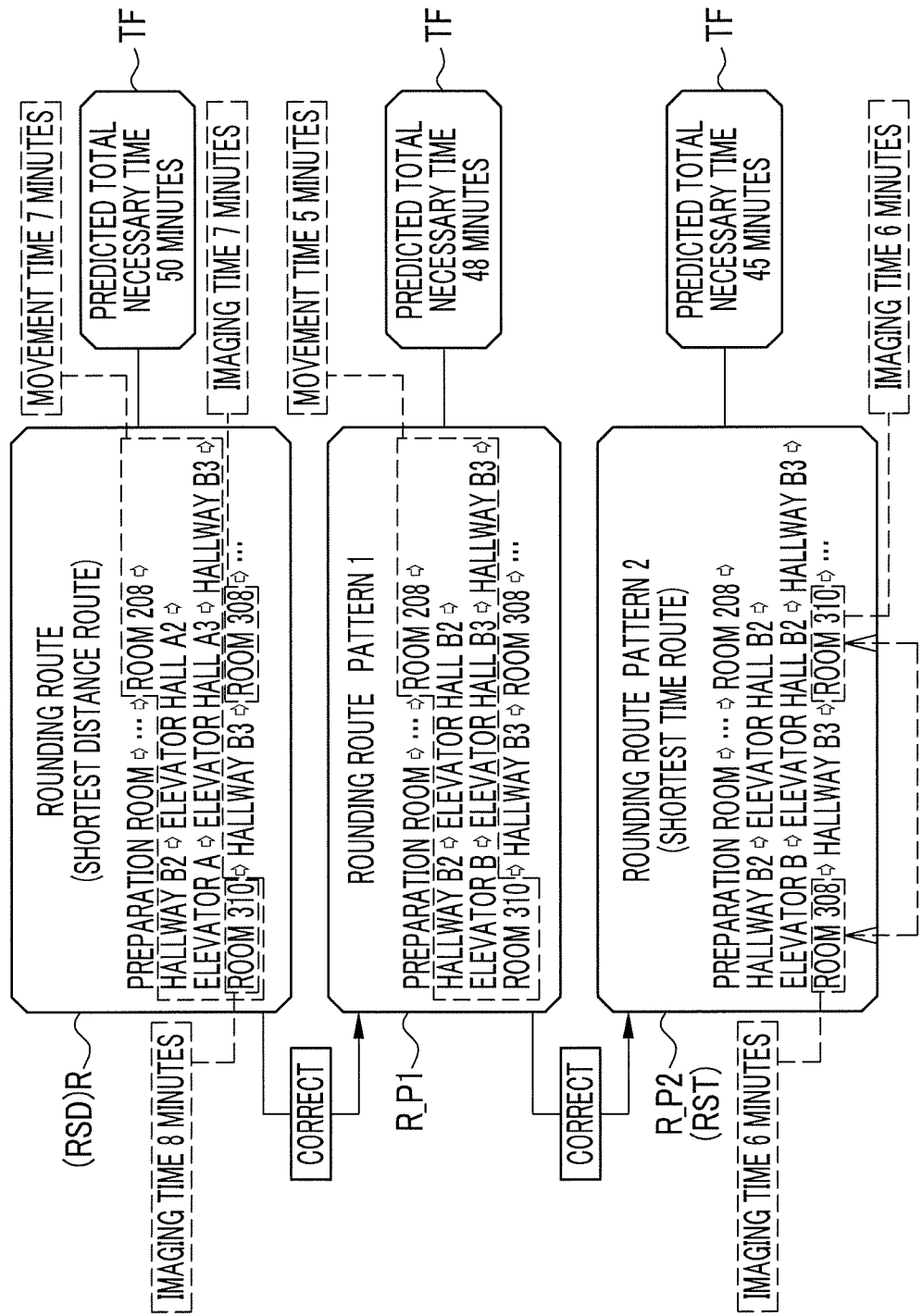
FIG. 17 is a diagram showing a state where a shortest time route is created in the creation unit.

In a second embodiment shown in FIGS. 15 to 17, time results data in which a time slot and an individual necessary time are registered in association with each other may be used.

As shown in FIG. 15, imaging time results data 70 of the present embodiment is data in which the imaging time TS is registered for each time slot. Further, as shown in FIG. 16, movement time results data 71 of the present embodiment is data in which the movement time TT is registered for each time slot. The time slot is a unit of 14 minutes such as "10:00-10:14" and "13:00-13:14". The time slot may be subdivided in a unit of a day of the week, a month, or the like.

In FIG. 15, for example, a case where the imaging time TS of the patient ID "P0001" and the imaging technique "simple imaging and chest front lying position" is "5 minutes" at a time slot of "10:00-10:14", "10:15-10:29", or the like, and is "10 minutes" at a time slot of "10:30-10:44", "13:00-13:14", or the like, is shown. As described above, the imaging time results data 70 is data in which the imaging time TS varies depending on the time slots. The reason why the imaging time TS varies depending on the time slots is because, for example, the availability status of the assistant AS varies depending on the time slots and the assistant AS may or may not perform assistance.

Further, in FIG. 16, a case where, for example, the movement time TT of the departure place "room 208", the transit place "hallway B2, elevator hall A2, elevator A, elevator hall A3, and hallway A3", and the arrival place "room 301" is "8 minutes" at the time slot of "10:00-10:14", or the like, "4 minutes" at the time slot of "10:15-10:29", or the like, and "5 minutes" at the time slot of "10:30-10:44", "13:00-13:14", or the like, is shown. As described above, the movement time results data 71 is data in which the movement time TT varies depending on the time slots. The reason why the movement time TT varies depending on the time slots is because, for example, the congestion level of the hospital varies depending on the time slots, as in a time slot where there are many visitors.

As shown in FIG. 17, the creation unit 51 first creates the shortest distance route RSD as the rounding route R, in a similar way to the above first embodiment. In addition, the creation unit 51 corrects the shortest distance route RSD in accordance with the imaging time TS and the movement time TT.

More specifically, the creation unit 51 determines whether there is a route having a shorter movement time TT in the routes between the rooms than in the case of the shortest distance route RSD. In a case where there is the route having the shorter movement time TT, the creation unit 51 replaces the route of the shortest distance route RSD with the route having the shorter movement time TT.

In FIG. 17, a case where the movement time TT of a route where an operator arrives at the room 310 from the room 208 through the hallway B2, the elevator hall A2, the elevator A, the elevator hall A3, and the hallway B3 is "7 minutes", in the shortest distance route RSD, is shown. Further, a case where the movement time TT of the route where an operator arrives at the room 310 from the room 208 through the hallway B2, the elevator hall B2, the elevator B, the elevator hall B3, and the hallway B3 at the same time slot is "5 minutes" is shown. In this case, the creation unit 51 replaces a route, of the movement time TT that is 7 minutes, where an operator arrives at the room 310 from the room 208 through the elevator A, in the shortest distance route RSD, with a route, of the movement time TT, where an operator arrives at the room 310 from the room 208 through the elevator B is "5 minutes, as indicated by a rounding route R_P1 of a pattern 1. By performing such correction, a predicted total necessary time TF of the rounding route R_P1 becomes "48 minutes" which is 2 minutes shorter than "50 minutes" of the predicted total necessary time TF of the shortest distance route RSD.

Further, the creation unit 51 determines whether or not there is a case where the imaging time TS and/or the movement time TT is shorter than in the case of the shortest distance route RSD in a case where an imaging order of radiography is changed and time slots are shifted. In a case where there is a case where the imaging time TS and/or the movement time TT is shorter, the creation unit 51 changes the imaging order of radiography.

In FIG. 17, in the shortest distance route RSD, a case where an imaging order is set so that radiography in the room 310 is first performed, and then, radiography in the room 308 is performed and the imaging times TS of radiography in the room 310 and the room 308 are "8 minutes" and "7 minutes", respectively, is shown. Further, a case where the imaging orders of radiography in the room 310 and radiography in the room 308 are switched and the time slots are shifted, imaging times TS of the radiography in the room 310 and the room 308 are respectively "6 minutes", is shown. In this case, the creation unit 51 changes the imaging order of the radiography so that the radiography in the room 308 is first performed and the radiography in the room 310 is performed later, as indicated by a rounding route R_P2 of a pattern 2. By performing such correction, a predicted total necessary time TF of the rounding route R_P2 becomes "45 minutes" which is 5 minutes shorter than "50 minutes" of the predicted total necessary time TF of the shortest distance route RSD, and is 3 minutes shorter than "48 minutes" of the predicted total necessary time TF of the rounding route R_P1.

The creation unit 51 creates the shortest time route RST in which the predicted total necessary time TF is the shortest as described above. The creation unit 51 outputs the shortest time route RST to the output controller 54 as the rounding route R. Since other processes are the same as in the first embodiment, description thereof will not be repeated. In FIG. 17, the rounding route R_P2 is the shortest time route RST.

As described above, in the second embodiment, the imaging time results data 70 in which a time slot and an imaging time TS are registered in association with each other, and the movement time results data 71 in which a time slot and a movement time TT are registered in association with each other are used. Further, the creation unit 51 creates the shortest time route RST where the predicted total necessary time TF becomes the shortest as the rounding route R. Accordingly, it is possible to complete rounding imaging earlier.

Further, the creation unit 51 creates the shortest distance route RSD and then modifies the shortest distance route RSD in accordance with the imaging time TS and the movement me TT, to thereby create the shortest time route RST. In other words, the creation unit 51 creates the shortest time route RST on the basis of the shortest distance route RSD. Accordingly, compared with a case where the shortest time route RST is derived from the rounding routes R of all patterns that can be considered by the imaging order information 14, it is possible to save much labor for creating the shortest time route RST.

Third Embodiment

Figure 18:
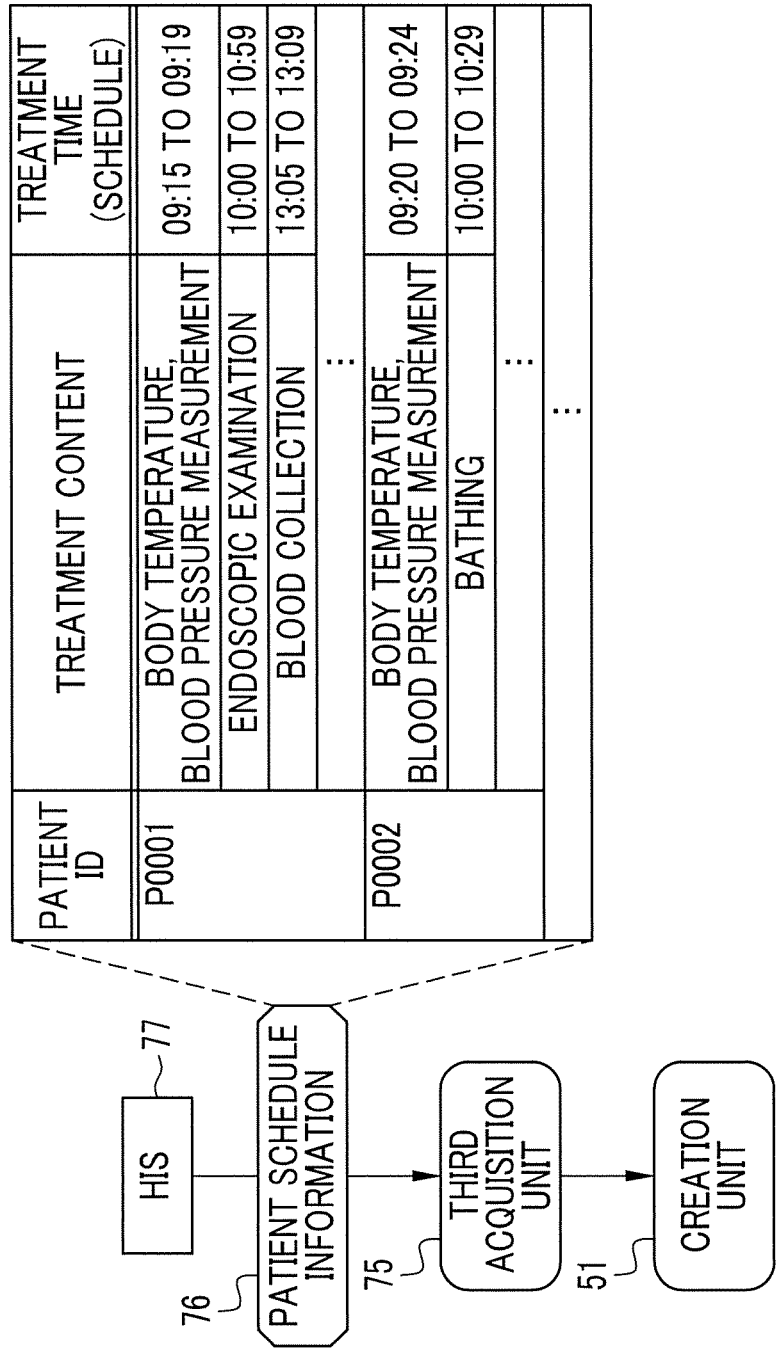
FIG. 18 is a diagram showing a third embodiment in which patient schedule information is acquired.
Figure 19:
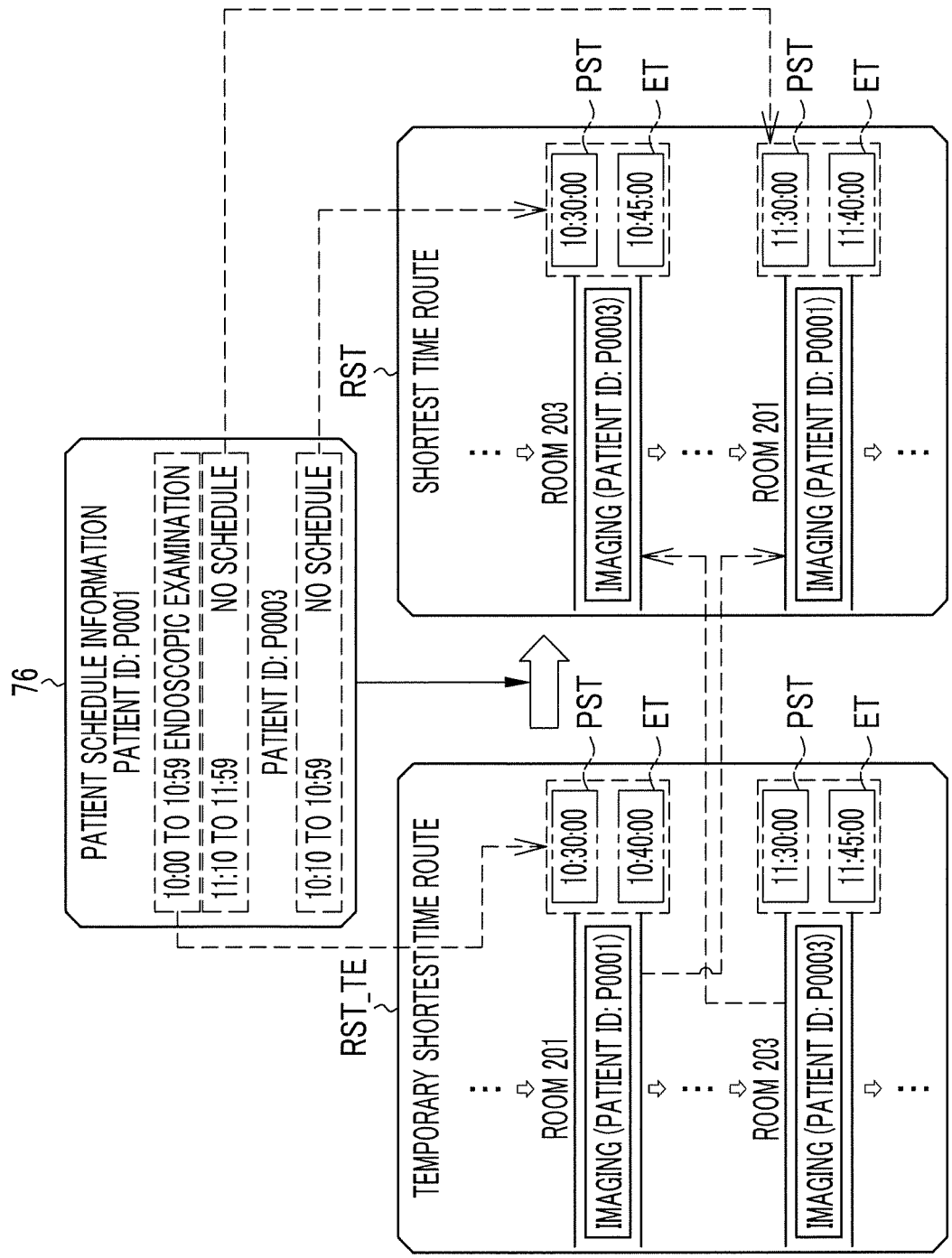
FIG. 19 is a diagram showing a state where a shortest time route is created with reference to patient schedule information in the creation unit.

In a third embodiment shown in FIGS. 18 and 19, patient schedule information 76 in which schedules of treatment for the patients P are registered is acquired, and the shortest time route RST is created with reference to the patient schedule information 76.

In FIG. 18, the third acquisition unit 75 acquires the patient schedule information 76. The third acquisition unit 75 outputs the acquired patient schedule information 76 to the creation unit 51.

The patient schedule information 76 is transmitted from a hospital information system (hereinafter, abbreviated as HIS (Hospital Information System)) 77 to the rounding imaging management apparatus 10 in accordance with, for example, a work start timing of a hospital. The patient schedule information 76 is information in which a treatment schedule for the patient P on a specific day is registered. More specifically, the patient schedule information 76 is information in which content of treatment and a scheduled treatment time are registered for each patient ID. The treatment includes general medical examination, ultrasonic examination, magnetic resonance imaging (MRI) examination, rehabilitation, and the like, in addition to body temperature measurement, blood pressure measurement, endoscopic examination, blood collection, and bathing shown in the figure.

As shown in FIG. 19, the creation unit 51 creates the shortest time route RST with reference to the patient schedule information 76 from the third acquisition unit 75. Specifically, the creation unit 51 creates the shortest time route RST from the shortest distance route RSD as described in the second embodiment. Further, the shortest time route RST is set as a temporary shortest time route RST_TE, and the temporary shortest time route RST_TE is corrected on the basis of the patient schedule information 76, so that the shortest time route RST to be finally output to the output controller 54 is created.

In FIG. 19, a case where a schedule of the patient P with the patient ID "P0001" registered in the patient schedule information 76 is endoscopic examination at a time slot of "10:00-10:59" and is no treatment at a time slot of "11:10-11:59", and a schedule of the patient P with the patient ID "P0003" is no treatment at a time slot of "10:00-10:59", is shown.
Further, a case where a scheduled start time PST of radiography of the patient P with the patient ID "P0001" in the temporary shortest time route RST_TE is "10:30:00" and a scheduled end time is "10:40:00" is shown. In this case, the endoscopic examination and the radiography of the patient P with the patient ID "P0001" are batting in the temporary shortest time route RST_TE. Accordingly, the creation unit 51 sets a radiography schedule of the patient P with the patient ID "P0001" to a time slot "11:10-11:59" where there is no other treatment schedule (scheduled start time "11:30:00" and scheduled end time "11:40:00"). Instead, a radiography schedule of the patient P with the patient ID "P0003" is changed to a time slot where the patient P with the patient ID "P0001" is originally scheduled to be radiographed, which is a time slot where there is no schedule for treatment of the patient P with the patient ID "P0003" (scheduled start time "10:30:00" and scheduled end time "10:45:00"), which is set as the shortest time route RST.

Thus, in the third embodiment, the third acquisition unit 75 acquires the patient schedule information 76, and the creation unit 51 creates the shortest time route RST with reference to the patient schedule information 76. Accordingly, it is possible to perform rounding imaging based on an actual situation.

Fourth Embodiment

Figure 20:
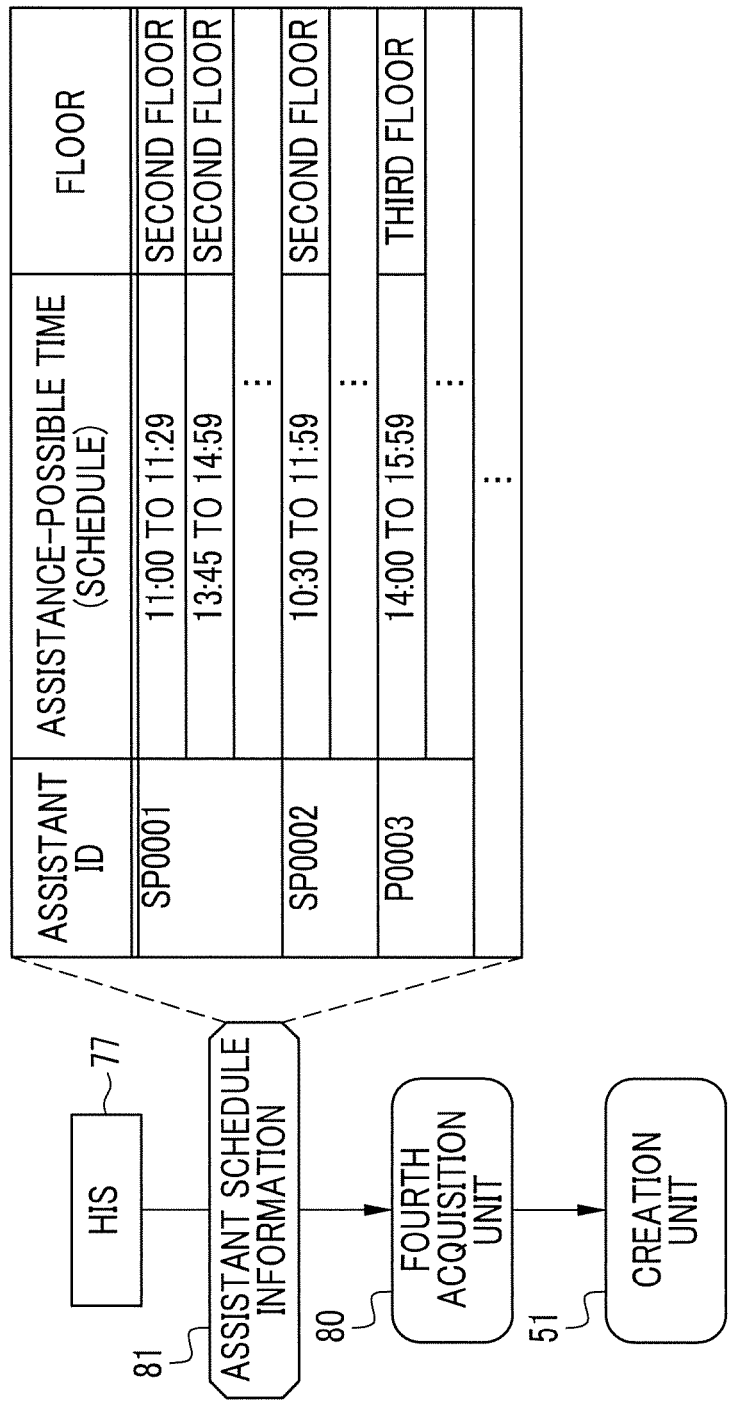
FIG. 20 is a diagram showing a fourth embodiment in which assistant schedule information is acquired.
Figure 21:
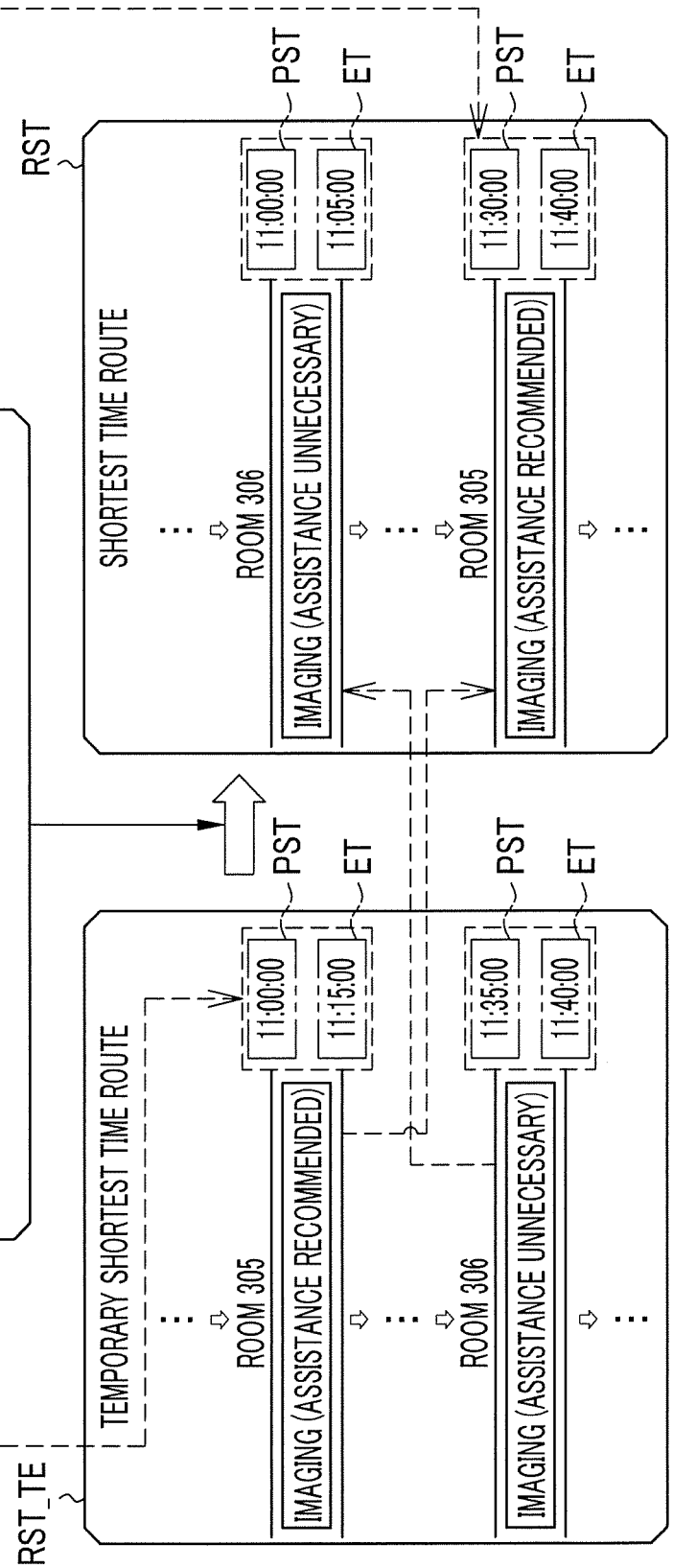
FIG. 21 is a diagram showing a state where a shortest time route is created with reference to assistant schedule information in the creation unit.

In a fourth embodiment shown in FIGS. 20 and 21, assistant schedule information 81 in which a schedule of the assistant AS is registered is acquired, and a shortest time route RST is created with reference to the assistant schedule information 81.

In FIG. 20, the fourth acquisition unit 80 acquires the assistant schedule information 81. The fourth acquisition unit 80 outputs the acquired assistant schedule information 81 to the creation unit 51.

The assistant schedule information 81 is transmitted from the HIS 77 to the rounding imaging management apparatus 10 in accordance with, for example, the work start timing of the hospital, similar to the patient schedule information 76 of the third embodiment. The assistant schedule information 81 is information in which the schedule of the assistant AS on a specific day is registered. More specifically, the assistant schedule information 81 is information in which a scheduled time and a floor at which assistance of radiography is possible are registered for each assistant ID for identifying each assistant AS.

As shown in FIG. 21, the creation unit 51 creates the shortest time route RST with reference to the assistant schedule information 81 from the fourth acquisition unit 80. Specifically, the creation unit 51 creates a temporary shortest time route RST_TE from the shortest distance route RSD as in the third embodiment. Further, by correcting the temporary shortest time route RST_TE on the basis of the assistant schedule information 81, the shortest time route RST to be finally output to the output controller 54 is created.

In FIG. 21, a case where, in the assistant schedule information 81, there is no assistant AS capable of performing assistance on the third floor at a time slot of "11:00-11:29" and an assistant AS with an assistant ID "SP0003" can perform assistance at a time slot of "11:30-11:59", is shown. Further, a case where a scheduled start time PST of radiography of a patient P recommended for assistance by the assistant AS in the temporary shortest time route RST_TE is "11:00:00", a scheduled end time is "11:15:00" and a scheduled start time PST of radiography of a patient P that does not need assistance is "11:35:00" and a scheduled end time is "11:40:00" is shown. In this case, in the temporary shortest time route RST_TE, the radiography recommended for assistance cannot help being performed without the assistant AS. Accordingly, the creation unit 51 sets a radiography schedule recommended for assistance to a time slot "11:30-11:59" where the assistant AS capable of performing assistance exists (scheduled start time "11:30:00" and scheduled end time "11:40:00"). Instead, a schedule of radiography that does not need assistance is changed to a time slot that has originally been a radiography schedule recommended for assistance (scheduled start time "11:00:00" and scheduled end time "11:05"00), which is then set as the shortest time route RST.

Thus, in the fourth embodiment, the fourth acquisition unit 80 acquires the assistant schedule information 81, and the creation unit 51 creates the shortest time route RST with reference to the assistant schedule information 81. Accordingly, it is possible to perform rounding imaging based on an actual situation.

In the rounding route R of the rounding plan display screen 65, the operator OP may be notified of the radiography recommended for assistance by marking or coloring the radiography recommended for assistance.

Figure 22:
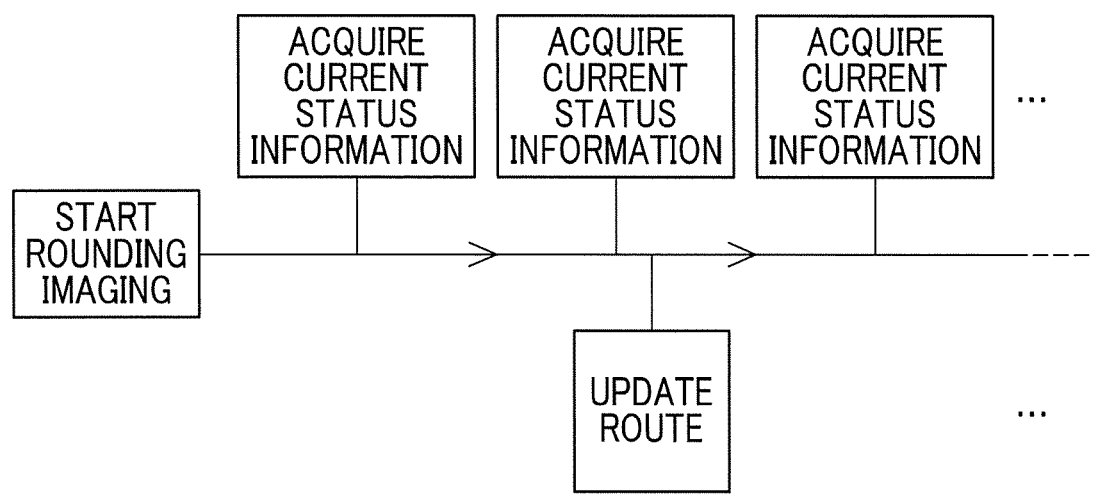
FIG. 22 is a diagram showing outlines of a fifth embodiment to an eighth embodiment.

In the following fifth to eighth embodiments, as outlined in FIG. 22, current status information 91 indicating a current status of information that is a basis for creating the rounding plan 16 is acquired during rounding imaging according to the shortest time route RST. In a case where the current status information 91 is content indicating that an individual necessary time is changed, the shortest time route RST is updated to be an updated shortest time route RST_UD, and the updated shortest time route RST_UD is output.

Fifth Embodiment

In the fifth embodiment shown in FIGS. 23 to 26, room occupancy status information 92 indicating a room occupancy status of a patient P for whom rounding imaging is to be performed in the hospital room 12 is acquired as the current status information 91. Further, an absence time TA of the patient P indicated as being absent in the room occupancy status information 92 is estimated, and the shortest time route RST is updated on the basis of the estimated absence time TA.

A timing for creating the rounding plan 16 is before the rounding imaging is started. For this reason, there may be a case where a sudden treatment is interrupted to the patient P during the rounding imaging and the patient P is not in the hospital room 12 at the time when radiography is scheduled in the rounding plan 16. Further, there may be a case where the patient P occasionally goes to the toilet and is not in the hospital room 12 at the time scheduled in the rounding plan 16. Accordingly, in the fifth embodiment, it is confirmed whether or not the patient P is absent in the hospital room 12 at the time when the radiography is scheduled in the rounding plan 16 on the basis of the room occupancy status information 92.

Figure 23:
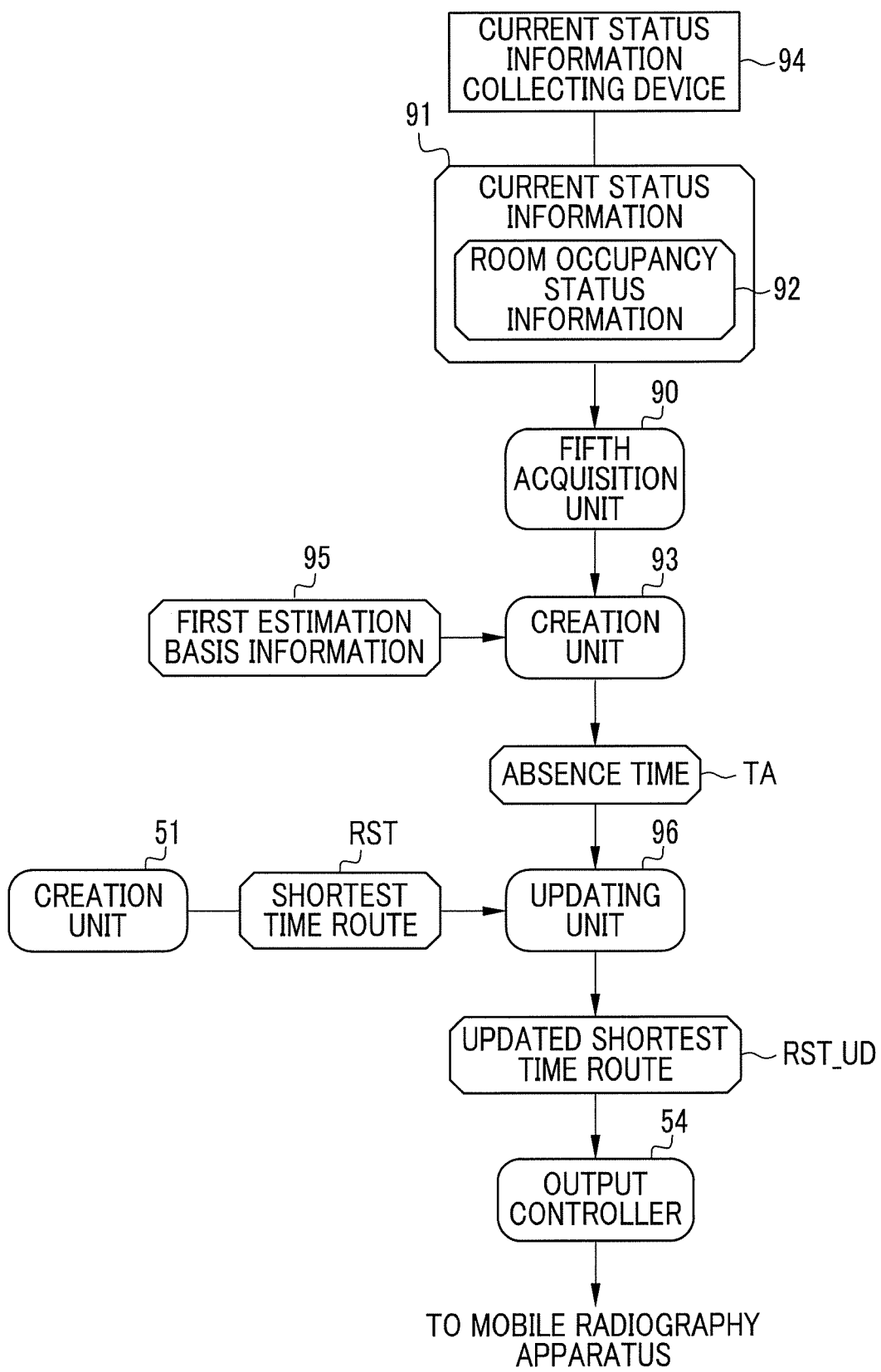
FIG. 23 is a diagram showing the fifth embodiment in which room occupancy status information is acquired to estimate a patient's absence time and a shortest time route is updated on the basis of the estimated absence time.

In FIG. 23, the fifth acquisition unit 90 acquires the current status information 91. The current status information 91 includes the room occupancy status information 92. The fifth acquisition unit 90 outputs the acquired current status information 91 to a first estimation unit 93.

The current status information 91 is transmitted from a current status information collecting device 94 to the rounding imaging management apparatus 10 at a regular timing such as every 5 minutes. The current status information collecting device 94 corresponds to the HIS 77 shown in the third and fourth embodiments, for example, determines whether or not the patient P currently undergoes another treatment in a place other than the hospital room 12, on the basis of the latest patient schedule information 76, and reflects the determination result in the room occupancy status information 92. Alternatively, the current status information collecting device 94 collects position information detected by a GPS function of a portable terminal possessed by the patient P, and determines a room occupancy status of the patient P and the reason in the case of absence (hereinafter, referred to as an absence reason). Further, by analyzing detection results of human sensors installed in major locations in the hospital, such as around beds in the hospital room 12, or videos of monitoring cameras installed in major locations in the hospital, the room occupancy status and absence reason of the patient P may be determined. In addition, the room occupancy status and the absence reason input by the patient P may be collected through the portable terminal possessed by the patient P. With respect to the patient P with a medical condition incapable of leaving the bed, except a case where the patient P undergoes another treatment at a place other than the hospital room 12, it may be determined that the patient P stays in the room.

The first estimation unit 93 estimates the absence time TA of the patient P indicated as being absent in the room occupancy status information 92 from the fifth acquisition unit 90, using the first estimation basis information 95. The first estimation unit 93 outputs the estimated absence time TA to an updating unit 96. The first estimation basis information 95 is stored in the storage device 30.

The updating unit 96 receives the shortest time route RST from the creation unit 51. The updating unit 96 updates the shortest time route RST on the basis of the absence time TA from the first estimation unit 93 to obtain an updated shortest time route RST_UD. The updating unit 96 outputs the updated shortest time route RST_UD to the output controller 54.

The output controller 54 outputs the updated shortest time route RST_UD to the mobile radiography apparatus 11. Specifically, the output controller 54 outputs the rounding plan display screen 65 in which the shortest time route RST is replaced with the updated shortest time route RST_UD to the mobile radiography apparatus 11.

As shown in FIG. 24, the room occupancy status information 92 is information in which the room occupancy status of the patient P and the absence reason are registered for each patient ID of the patient P for whom rounding imaging is to be performed. The absence reason is not registered in a case where the room occupancy status is "presence", and is registered only in a case where the room occupancy status is "absence". In FIG. 24, the room occupancy status information 92 in which "absence" is registered as the room occupancy status of the patient P with the patient ID "P0001" and "general medical examination" is registered as the absence reason, and "presence" is registered as the room occupancy status of the patient P with the patient ID "P0002" is shown.

As shown in FIG. 25, the first estimation basis information 95 is information in which the absence time TA corresponding to the absence reason is registered. The absence reason includes "endoscopic examination", "MRI examination", "rehabilitation", "restroom", "purchasing", "visit", "bathing", and the like, in addition to "general medical examination" shown in FIG. 24. The absence time TA is a value obtained by measuring the past absence time TA for each absence reason, for example, in a similar way to the necessary time T and derived on the basis of the measured past absence time TA. As an example, in a method for deriving the absence time TA of the absence reason "purchasing", times taken for past purchases of a plurality of patients P selected at random are measured and collected. Further, an average value of the collected times is set as the absence time TA of the absence reason "purchasing".

Figure 26:
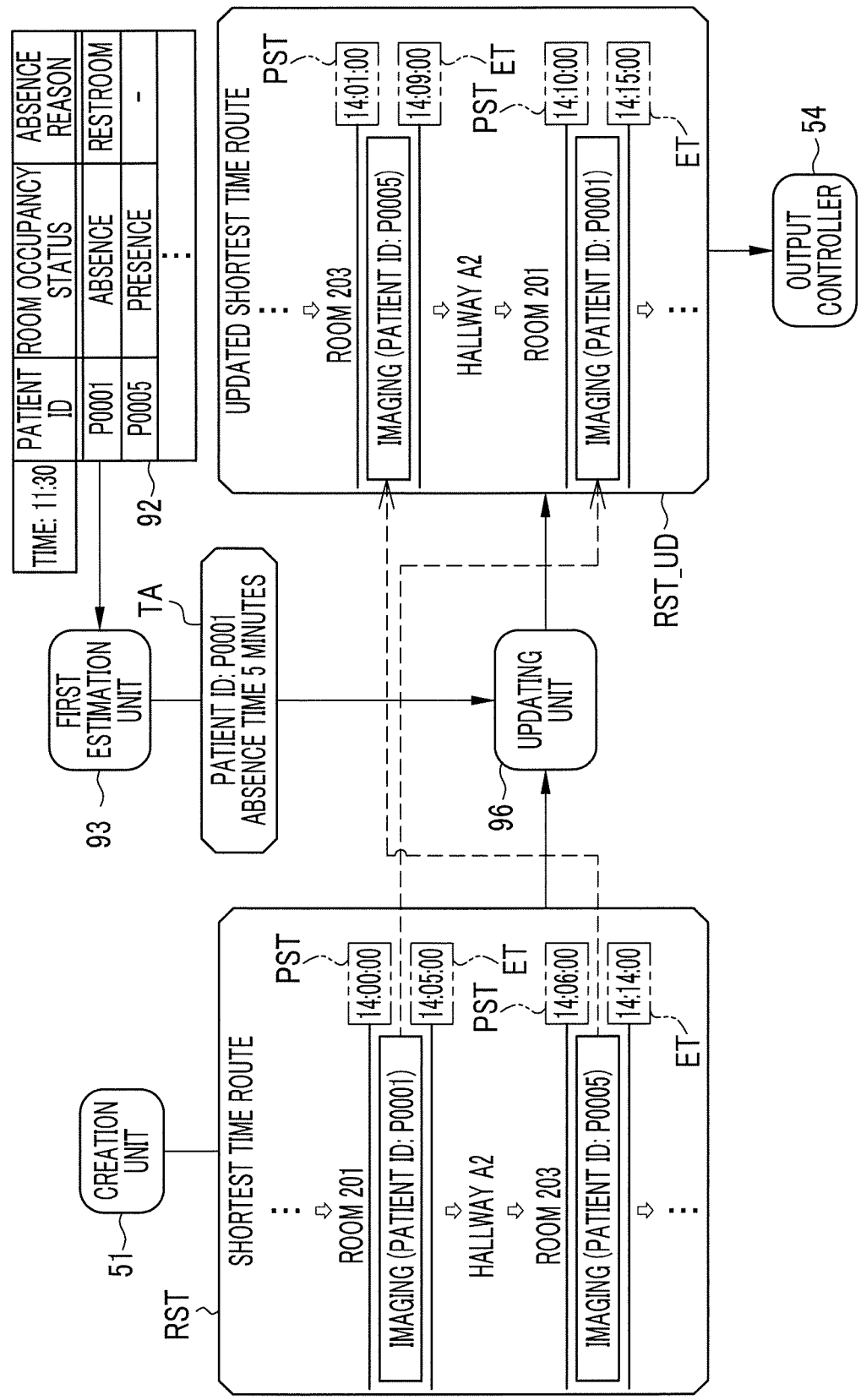
FIG. 26 is a diagram showing a state where the shortest time route is set to an updated shortest time route on the basis of an absence time in an updating unit.

FIG. 26 shows a state where the shortest time route RST is set as the updated shortest time route RST_UD on the basis of the absence time TA. In FIG. 26, in the room occupancy status information 92 at time "11:30", a case where "absence" is registered as the room occupancy status of the patient P with the patient ID "P0001" and the absence reason is registered as "bating", and "presence" is registered as the room occupancy status of the patient P with the patient ID "P0005" is shown. Further, a case where the first estimation unit 93 estimates that the absence time TA of the patient P with the patient ID "P0001" is "five minutes" is shown. In addition, a case where the scheduled start time PST of radiography of the patient P with the patient ID "P0001" is "11:30:00" and the scheduled start time PST of radiography of the patient P with the patient ID "P0005" is "11:42:00", in the shortest time route RST created in the creation unit 51, is shown. In this case, the updating unit 96 switches the imaging order of radiography of the patient P with the patient ID "P0001" and the patient P with the patient ID "P0005", and outputs the updated shortest time route RST_UD updated so that the radiography of the patient P with the patient ID "P0005" is performed first while the patient P with the patient ID "P0001" is absent.

As described above, in the fifth embodiment, the fifth acquisition unit 90 acquires the room occupancy status information 92 indicating the room occupancy status of the patient P for whom rounding imaging is to be performed in the hospital room 12. The first estimation unit 93 estimates the absence time TA of the patient P indicated as being absent in the room occupancy status information 92. The updating unit 96 updates the shortest time route RST on the basis of the absence time TA to obtain the updated shortest time route RST_UD. The output controller 54 outputs the updated shortest time route RST_UD. Accordingly, a wasteful waiting time such as waiting for the patient P to return to the hospital room 12 does not occur, and thus, it is possible to smoothly advance rounding imaging.

The room occupancy status information 92 may be transmitted from the current status information collecting device 94 to the rounding imaging management apparatus 10 at a timing when the room occupancy status of the patient P is changed. Further, a message for prompting the patient P to return to the room may be output from the output controller 54 to the portable terminal of the patient P indicated as being absent in the room occupancy status information 92.

The rounding imaging management apparatus 10 may perform the functions of the current status information collecting device 94. This is similarly applied to the following sixth to eighth embodiments.

Sixth Embodiment

In the sixth embodiment shown in FIGS. 27 to 30, treatment status information 100 indicating a treatment status in a hospital room 12 of a patient P for whom rounding imaging is to be performed is acquired as the current status information 91. Further, in a case where the treatment status information 100 represents that treatment is performed in the hospital room 12, the treatment time TM to be taken for the treatment is estimated, and the shortest time route RST is updated on the basis of the estimated treatment time TM.

Similar to the fifth embodiment, a case where a sudden treatment is interrupted to the patient P in the middle of rounding imaging and the patient P is treated in the hospital room 12 at a timing when radiography is scheduled in the rounding plan 16 may be considered. Accordingly, in the sixth embodiment, at the timing when the radiography is scheduled in the rounding plan 16, it is confirmed whether or not the patient P is treated in the hospital room 12 from the treatment status information 100.

Figure 27:
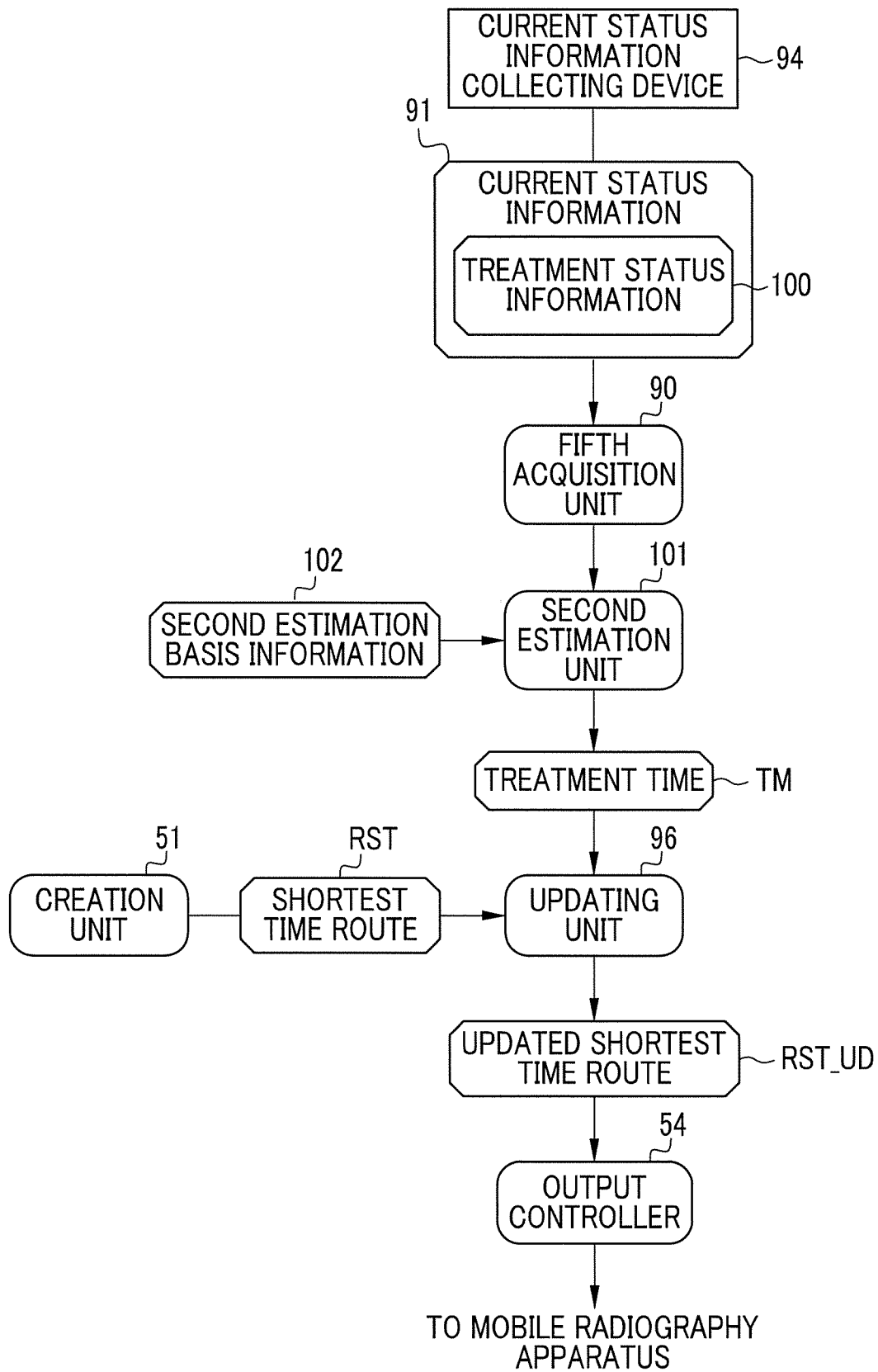
FIG. 27 is a diagram showing the sixth embodiment in which treatment status information is acquired to estimate a treatment time for treatment and the shortest time route is updated on the basis of the estimated treatment time.

In FIG. 27, the fifth acquisition unit 90 acquires the current status information 91 including the treatment status information 100. The current status information collecting device 94 corresponds to the HIS 77 as in the case of the fifth embodiment, and determines whether or not the patient P currently undergoes another treatment in the hospital room 12, on the basis of the latest patient schedule information 76, for example, and reflects the determination result in the treatment status information 100. Alternatively, the current status information collecting device 94 may collect, through a portable terminal possessed by the patient P, a nurse who treats the patient P, or the like, a treatment status and treatment content input by the patient P, the nurse, or the like.

The second estimation unit 101 estimates the treatment time TM to be taken for treatment using the second estimation basis information 102 in a case where the treatment status information 100 from the fifth acquisition unit 90 represents that the treatment is being performed in the hospital room 12. The second estimation unit 101 outputs the estimated treatment time TM to the updating unit 96. The second estimation basis information 102 is stored in the storage device 30.

The updating unit 96 updates the shortest time route RST from the creation unit 51 on the basis of the treatment time TM from the second estimation unit 101 to obtain an updated shortest time route RST_UD. Since subsequent processes are the same as in the fifth embodiment, description thereof will not be repeated.

Figure 28:
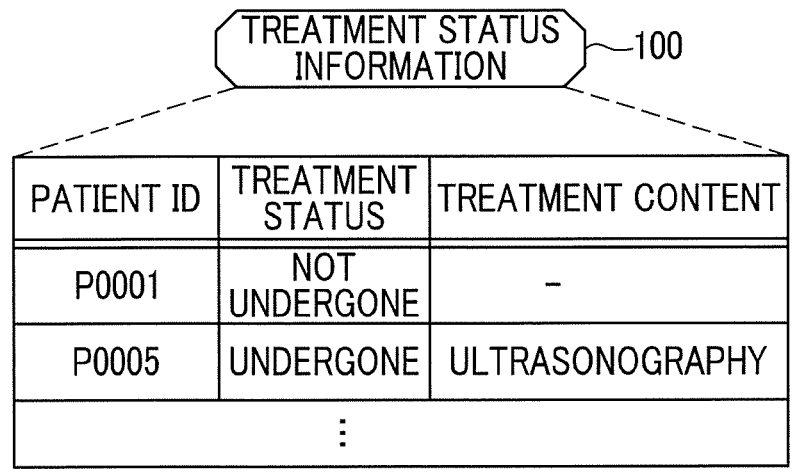
FIG. 28 is a diagram showing treatment situation information.

As shown in FIG. 28, the treatment status information 100 is information in which the treatment status and treatment content in the hospital room 12 of the patient P are registered for each patient ID of the patient P for whom rounding imaging is to be performed. In FIG. 28, a case where the treatment status information 100 in which "not undergone" is registered as the treatment status of the patient P with the patient ID "P0001", "undergone" is registered as the treatment status of the patient P with the patient ID "P0005", and "ultrasonography" is registered as the treatment content is shown.

Figure 29:
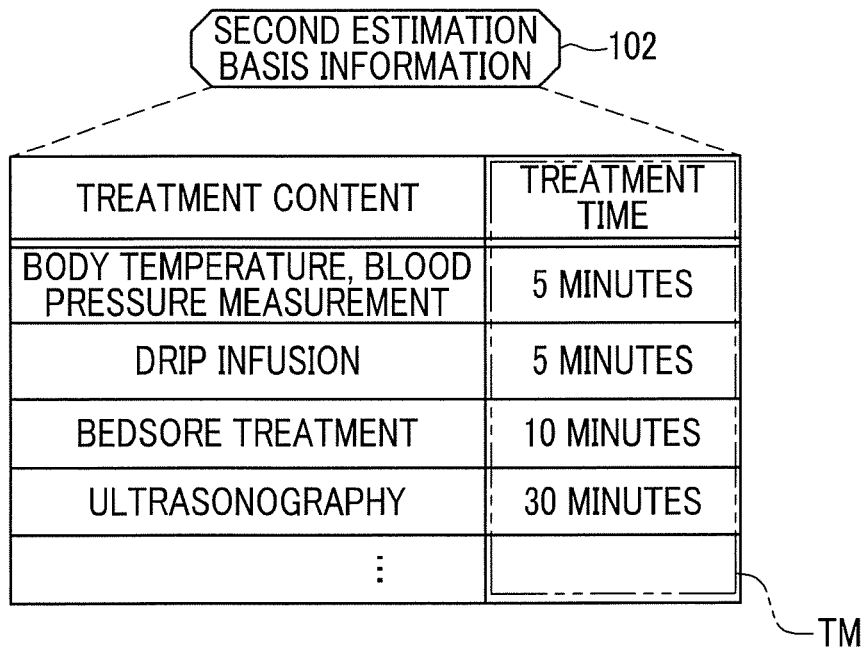
FIG. 29 is a diagram showing second estimation basis information.

As shown in FIG. 29, the second estimation basis information 102 is information in which the treatment time TM corresponding to the treatment content is registered. The treatment content includes "body temperature and blood pressure measurement", "drip infusion", "bedsore treatment", and the like, in addition to the "ultrasonography" shown in FIG. 28. Similar to the absence time TA, the treatment time TM is a value obtained by measuring the past treatment time TM for each treatment content and derived on the basis of the measured past treatment time TM.

Figure 30:
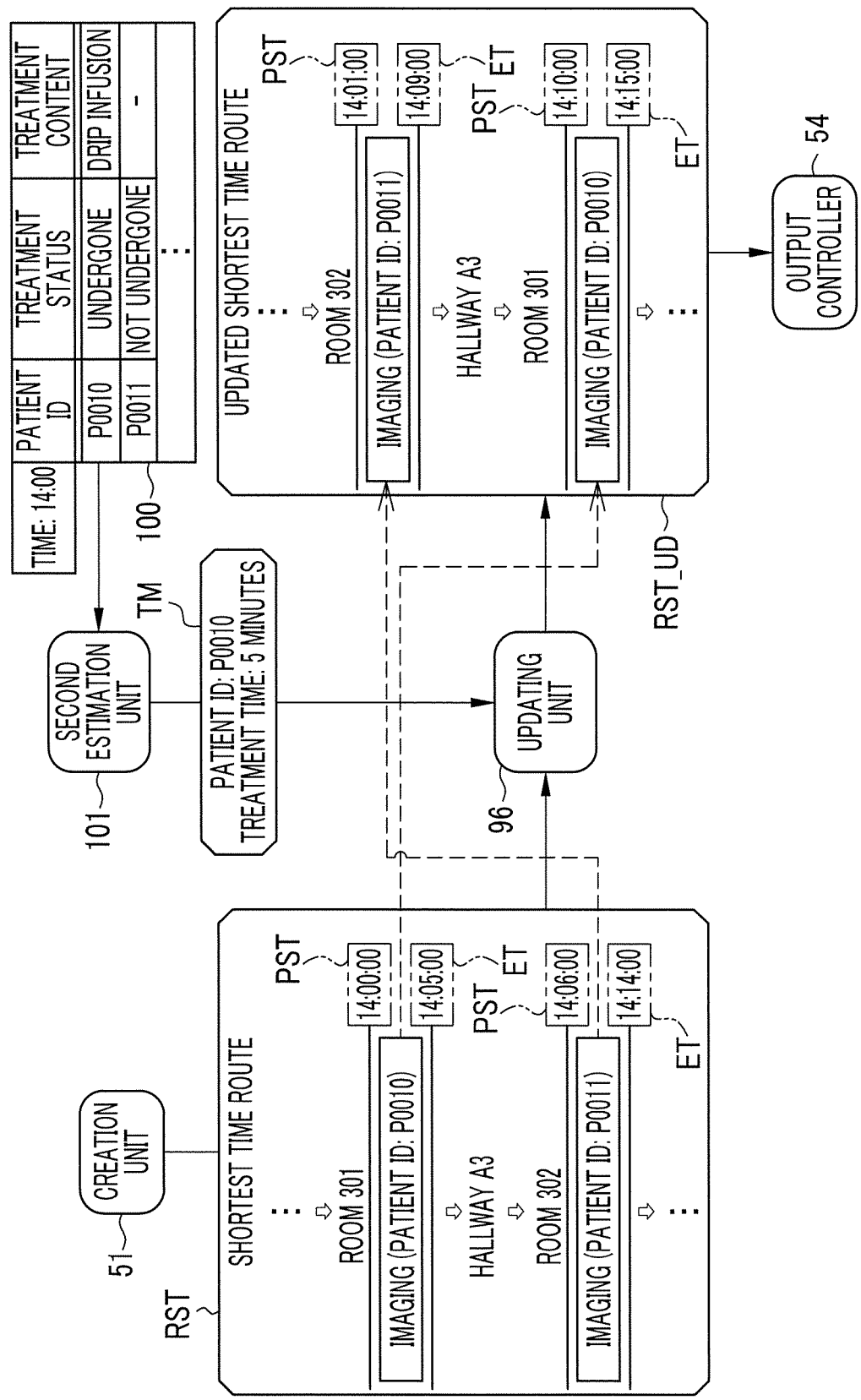
FIG. 30 is a diagram showing a state where the shortest time route is set to the updated shortest time route on the basis of the treatment time in the updating unit.

FIG. 30 shows a state where the shortest time route RST is set as the updated shortest time route RST_UD on the basis of the treatment time TM, in the updating unit 96. FIG. 30 shows a case where the treatment status information 100 in which "undergone" is registered as the treatment status of the patient P with the patient ID "P0010", "drip infusion" is registered as the treatment content, and "not undergone" is registered as the treatment status of the patient P with the patient ID "P0011", and "ultrasonography" is registered as the treatment content. Further, the second estimation unit 101 shows a case where the treatment time TM of the patient P with the patient ID "P0010" is estimated as "five minutes". Further, a case where, in the shortest time route RST created in the creation unit 51, the scheduled start time PST of radiography of the patient P with the patient ID "P0010" is "14:00:00" and the scheduled start time PST of radiography of the patient P with the patient ID "P0011" is "14:06:00", is shown. In this case, the updating unit 96 switches the imaging order of radiography of the patient P with the patient ID "P0010" and the patient P with the patient ID "P0011", and outputs the updated shortest time route RST_UD updated so that the radiography of the patient P with the patient ID "P0011" is performed first while drip infusion treatment is performed for the patient P with the patient ID "P0010".

As described above, in the sixth embodiment, the fifth acquisition unit 90 acquires the treatment status information 100 representing the treatment status in the hospital room 12 for the patient P for whom rounding imaging is to be performed. The second estimation unit 101 estimates the treatment time TM to be taken for treatment in a case where the treatment status information 100 indicates that treatment is being performed in the hospital room 12. The updating unit 96 updates the shortest time route RST on the basis of the treatment time TM to obtain the updated shortest time route RST_UD. The output controller 54 outputs the updated shortest time route RST_UD. Accordingly, it is possible to smoothly advance rounding imaging without generating a wasteful waiting time such as waiting for the end of the treatment of the patient P in the hospital room 12.

The treatment status information 100 may be transmitted from the current status information collecting device 94 to the rounding imaging management apparatus 10 at a timing when the treatment status of the patient P is changed.

Seventh Embodiment

Figure 31:
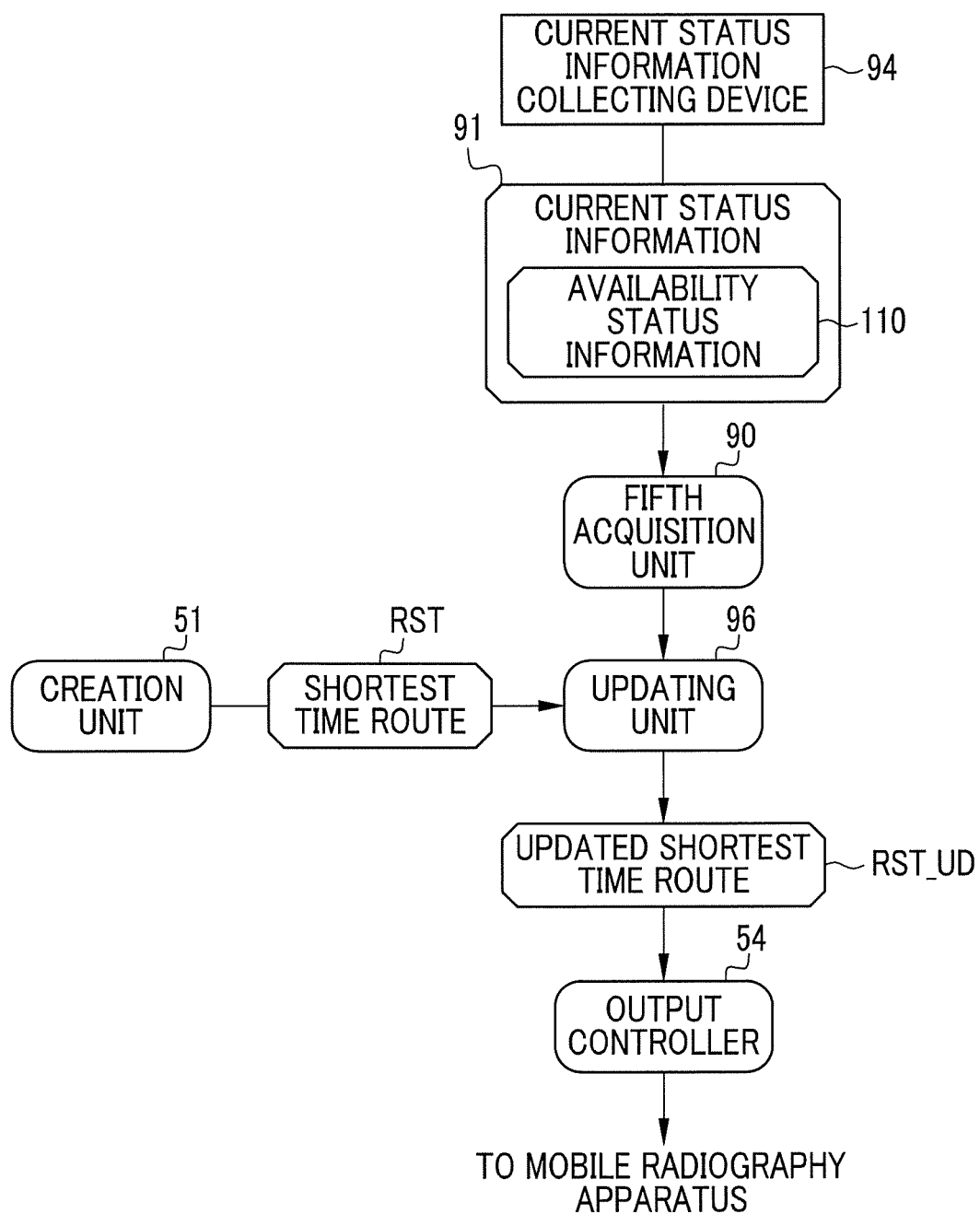
FIG. 31 is a diagram showing the seventh embodiment in which availability status information is acquired and the shortest time route is updated on the basis of the availability status information.
Figure 32:
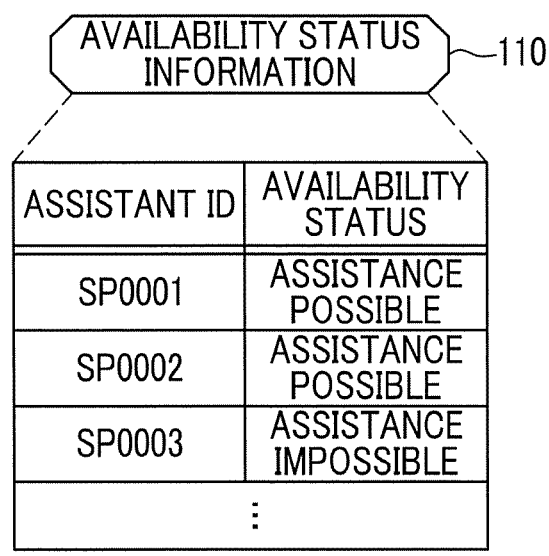
FIG. 32 is a diagram showing availability status information.
Figure 33:
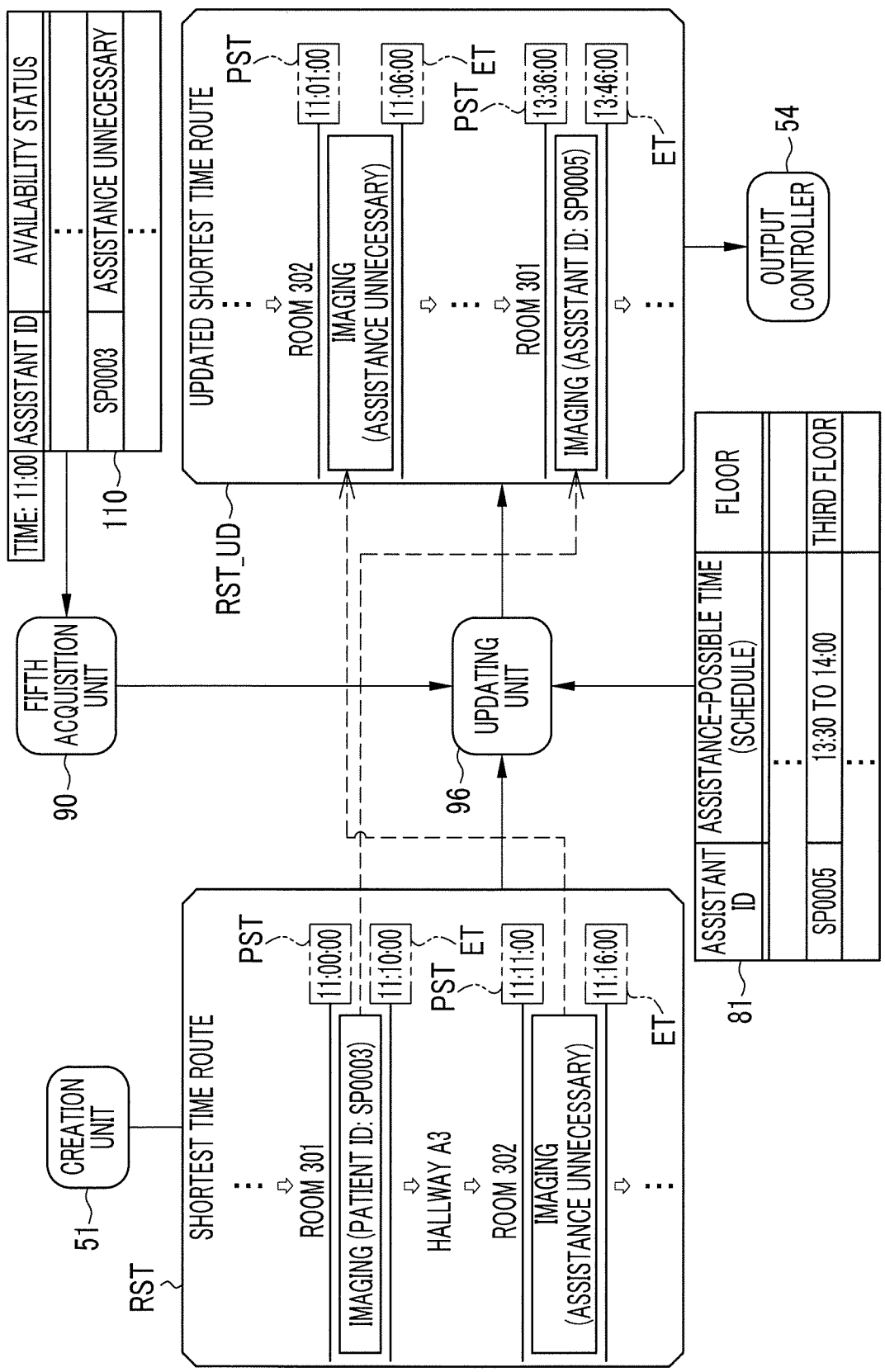
FIG. 33 is a diagram showing a state where the shortest time route is set to the updated shortest time route on the basis of the availability status information in the updating unit.

In the seventh embodiment shown in FIGS. 31 to 33, availability status information 110 indicating an availability status of an assistant AS is acquired as the current status information 91. Further, on the basis of the availability status information 110, the shortest time route RST is updated.

The availability status of the assistant AS is flexible in a similar way to the room occupancy status and the treatment status of the patient P. Accordingly, in creation of the rounding plan 16, there may be a case where the assistant AS cannot perform assistance due to a sudden change in a schedule in performing radiography scheduled to be assisted by the assistant AS. Accordingly, in the seventh embodiment, at the time of radiography scheduled to be assisted by the assistant AS in the rounding plan 16, it is confirmed whether or not the assistant AS can actually perform assistance from the availability status information 110.

In FIG. 31, the fifth acquisition unit 90 acquires the current status information 91 including the availability status information 110. The fifth acquisition unit 90 outputs the acquired current status information 91 to the updating unit 96. The current status information collecting device 94 corresponds to the HIS 77 as in the case of the fifth and sixth embodiments, for example, and determines the availability status of the assistant AS on the basis of the latest assistant schedule information 81 and reflects the determination result in the availability status information 110. Alternatively, the current status information collecting device 94 may collect position information detected by the GPS function of a portable terminal possessed by the assistant AS, and determines the availability status of the assistant AS on the basis of the collected position information. Specifically, in a case where the assistant AS is at a nurse station, it is determined that assistance is possible, and in a case where the assistant AS is in a hospital room 12 other than the hospital room 12 of the patient P who is scheduled to be assisted, it is determined that the assistance is not possible. Further, the availability status of the assistant AS may be determined by analyzing videos of monitoring cameras installed in main locations in the hospital. In addition, the availability status input by the assistant AS may be collected through the portable terminal possessed by the assistant AS.

The updating unit 96 updates the shortest time route RST from the creation unit 51 on the basis of the availability status information 110 from the fifth acquisition unit 90 to obtain the updated shortest time route RST_UD. Since subsequent processes are the same as in the fifth and sixth embodiments, description thereof will not be repeated.

As shown in FIG. 32, the availability status information 110 is information in which an availability status is registered for each assistant ID. FIG. 32 shows an example of the availability status information 110 in which "assistance possible" is registered as availability statuses of assistants AS with assistant IDs "SP0001" and "SP0002" and "assistance impossible" is registered as an availability status of an assistant AS with an assistant ID "SP0003".

FIG. 33 shows a state where the updating unit 96 sets the shortest time route RST as the updated shortest time route RST_UD on the basis of the availability status information 110. FIG. 33 shows a case where in the availability status information 110 at time "11:00", "assistance impossible" is registered as the availability status of the assistant AS with the assistant ID "SP0003". Further, a case where, in the shortest time route RST created by the creation unit 51, a radiography start scheduled time PST scheduled to be assisted by the assistant AS of the assistant ID "SP0003" is "11:00:00" and a radiography start scheduled time PST that does not need assistance is "11:11:00", is shown. Further, in the assistant schedule information 81, a case where "13:30-14:00" is registered at a time at which assistance is available on the third floor of an assistant AS with an assistant ID "SP0005" is shown. In this case, the updating unit 96 performs radiography first that does not need assistance, and outputs the updated shortest time route RST_UD updated so as to perform radiography recommended for assistance at a time slot of "13:30-14:00" at which the assistant AS with the assistant ID "SP0005" can perform assistance.

As described above, in the seventh embodiment, the fifth acquisition unit 90 acquires the availability status information 110 indicating the availability status of the assistant AS. The updating unit 96 updates the shortest time route RST on the basis of the availability status information 110 to obtain the updated shortest time route RST_UD. The output controller 54 outputs the updated shortest time route RST_UD. Thus, a wasteful waiting time such as waiting for the assistant AS capable of performing assistance does not occur, and thus, it is possible to perform radiography without help from the assistant AS, to thereby prevent the imaging time TS from being prolonged. Accordingly, it is possible to smoothly advance rounding imaging.

The availability status information 110 may be transmitted from the current status information collecting device 94 to the rounding imaging management apparatus 10 at a timing when the availability status of the assistant AS is changed.

In a case where the scheduled assistant AS is not able to perform assistance, a message asking for assistance may be output from the output controller 54 to a portable terminal of another assistant AS. In this case, another assistant AS in a setting area centering around the hospital room 12 where radiography is recommended for assistance is determined from the position information detected by the GPS function of a portable terminal of the assistant AS, and a message may be output limitedly to the portable terminal of the determined assistant AS.

Eighth Embodiment

Figure 34:
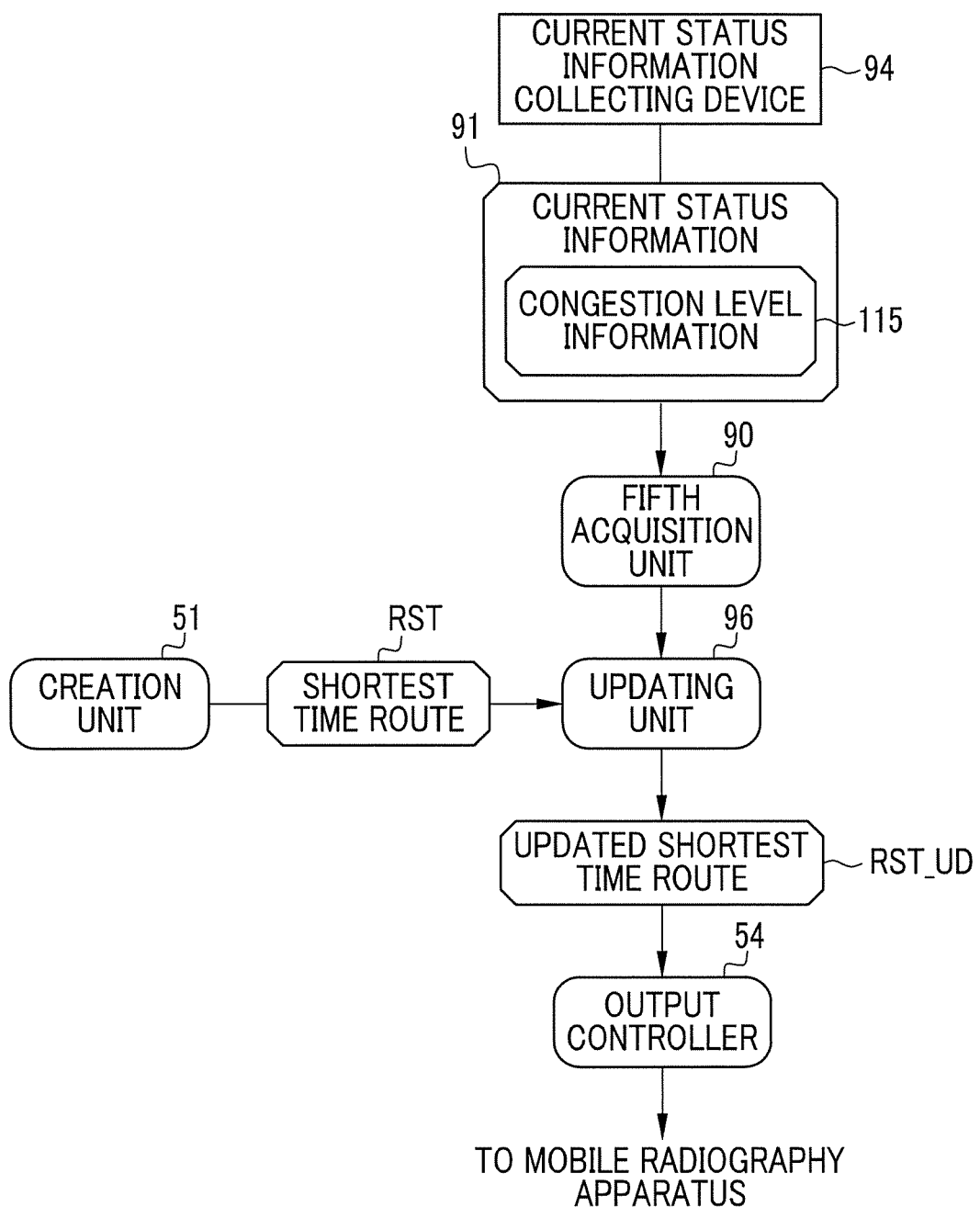
FIG. 34 is a diagram showing an eighth embodiment in which congestion level information is acquired and the shortest time route is updated on the basis of the congestion level information.
Figure 35:
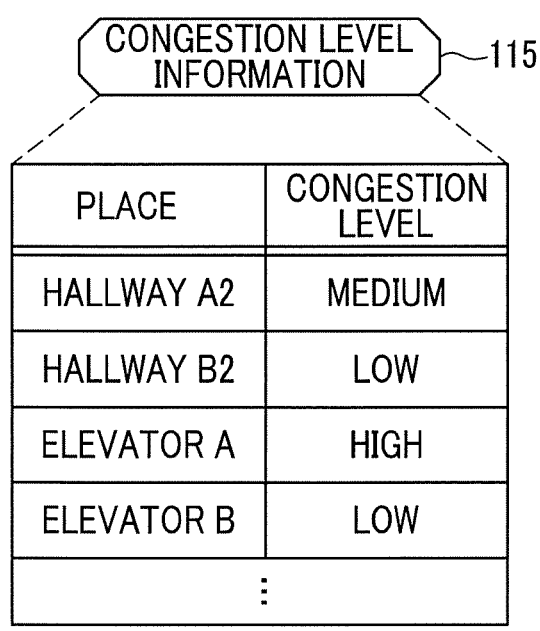
FIG. 35 is a diagram showing congestion level information.
Figure 36:
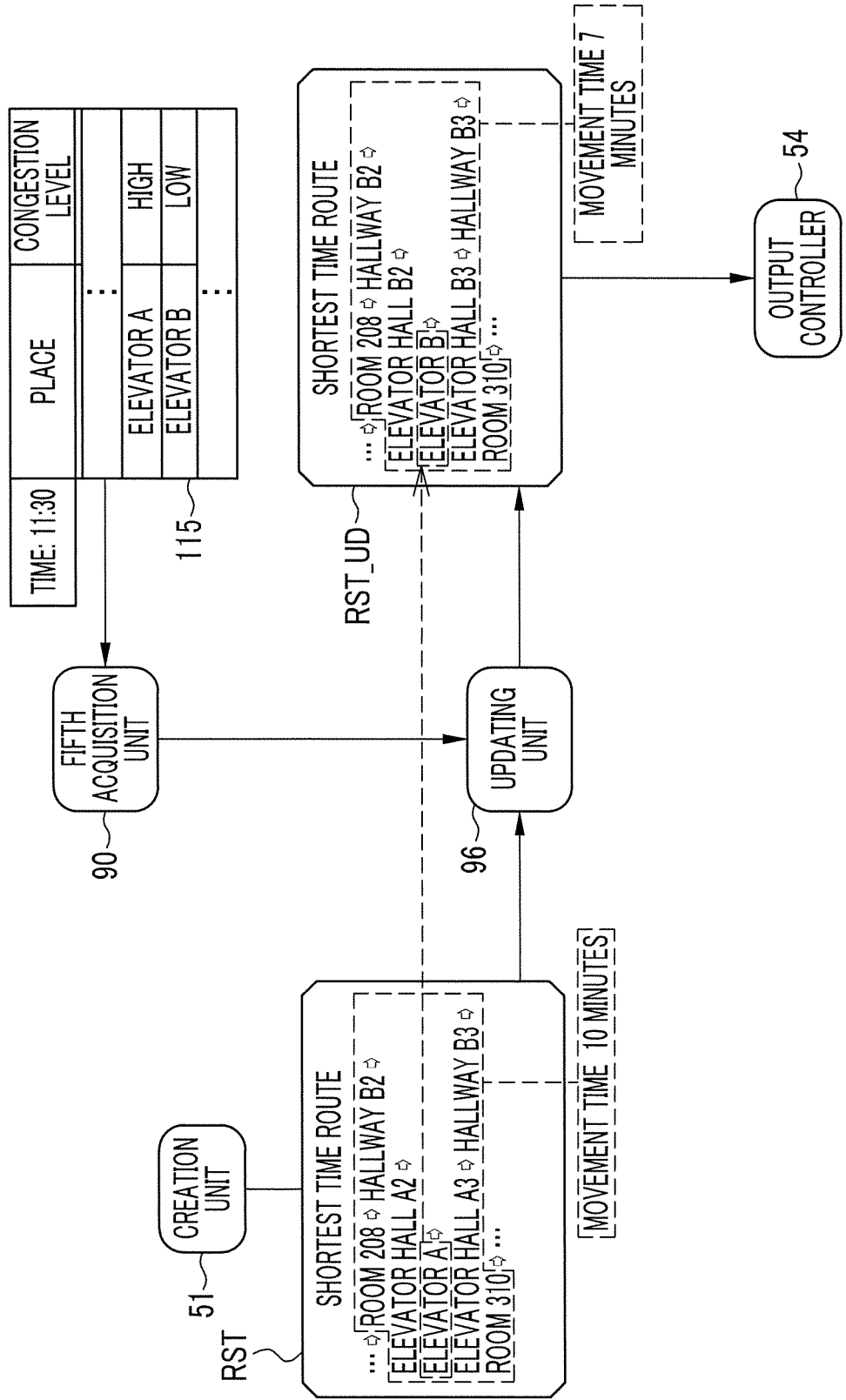
FIG. 36 is a diagram showing a state where the shortest time route is set to the updated shortest time route on the basis of the congestion level information in the updating unit.

In an eighth embodiment shown in FIGS. 34 to 36, congestion level information 115 indicating a congestion level of a hospital is acquired as the current status information 91. Further, on the basis of the congestion level information 115, the shortest time route RST is updated.

The congestion level of the hospital also changes from moment to moment, in a similar way to the room occupancy status of the patient P, the treatment status, and the availability status of the assistant AS. Accordingly, in the eighth embodiment, the congestion level of the current hospital is confirmed by the congestion level information 115.

In FIG. 34, the fifth acquisition unit 90 acquires the current status information 91 including the congestion level information 115. The fifth acquisition unit 90 outputs the acquired current status information 91 to the updating unit 96. For example, the current status information collecting device 94 analyzes videos of monitoring cameras installed in main locations in the hospital to determine a congestion level. Further, the current status information collecting device 94 collects facility information including an operating state or the like of an elevator, and determines the congestion level on the basis of the collected facility information.

The updating unit 96 updates the shortest time route RST from the creation unit 51 on the basis of the congestion level information 115 from the fifth acquisition unit 90 to obtain the updated shortest time route RST_UD. Since subsequent processes are the same as in the fifth to seventh embodiments, description thereof will not be repeated.

As shown in FIG. 35, the congestion level information 115 is information in which a congestion level is registered for each hospital location. FIG. 35 shows an example of the congestion level information 115 in which "medium" is registered as the congestion level of the hallway A2, "low" is registered as the congestion level of the hallway B2 and the elevator B, and "high" is registered as the congestion level of the elevator A.

FIG. 36 shows a state where the updating unit 96 sets the shortest time route RST as the updated shortest time route RST_UD on the basis of the congestion level information 115. In FIG. 36, a case where "high" is registered as the congestion level of the elevator A and "low" is registered as the congestion level of the elevator B in the congestion level information 115 at time "11:00" is shown. Further, a case where there is a route where it takes 10 minutes as the movement time TT from the room 208 to the room 310 through the elevator A in the shortest time route RST created by the creation unit 51, is shown. In this case, the updating unit 96 outputs the updated shortest time route RST_UD obtained by replacing the route from the room 208 to the room 310 through the elevator A with a route where it takes 7 minutes as the movement time TT from the room 208 to the room 310 through the elevator B.

As described above, in the eighth embodiment, the fifth acquisition unit 90 acquires the congestion level information 115 indicating the congestion level of the hospital. The updating unit 96 updates the shortest time route RST on the basis of the congestion level information 115 to obtain the updated shortest time route RST_UD. The output controller 54 outputs the updated shortest time route RST_UD. Accordingly, it is possible to smoothly advance rounding imaging without prolonging the movement time TT due to congestion at a place where the congestion level is "high" at present.

The congestion level information 115 may be transmitted from the current status information collecting device 94 to the rounding imaging management apparatus 10 at a timing when the congestion level of the hospital is changed.

As described above, the fifth to eighth embodiments have been described as the embodiments for updating the shortest time route according to the current status information 91, but the fifth to eighth embodiments may be executed in combination.

Figure 37:
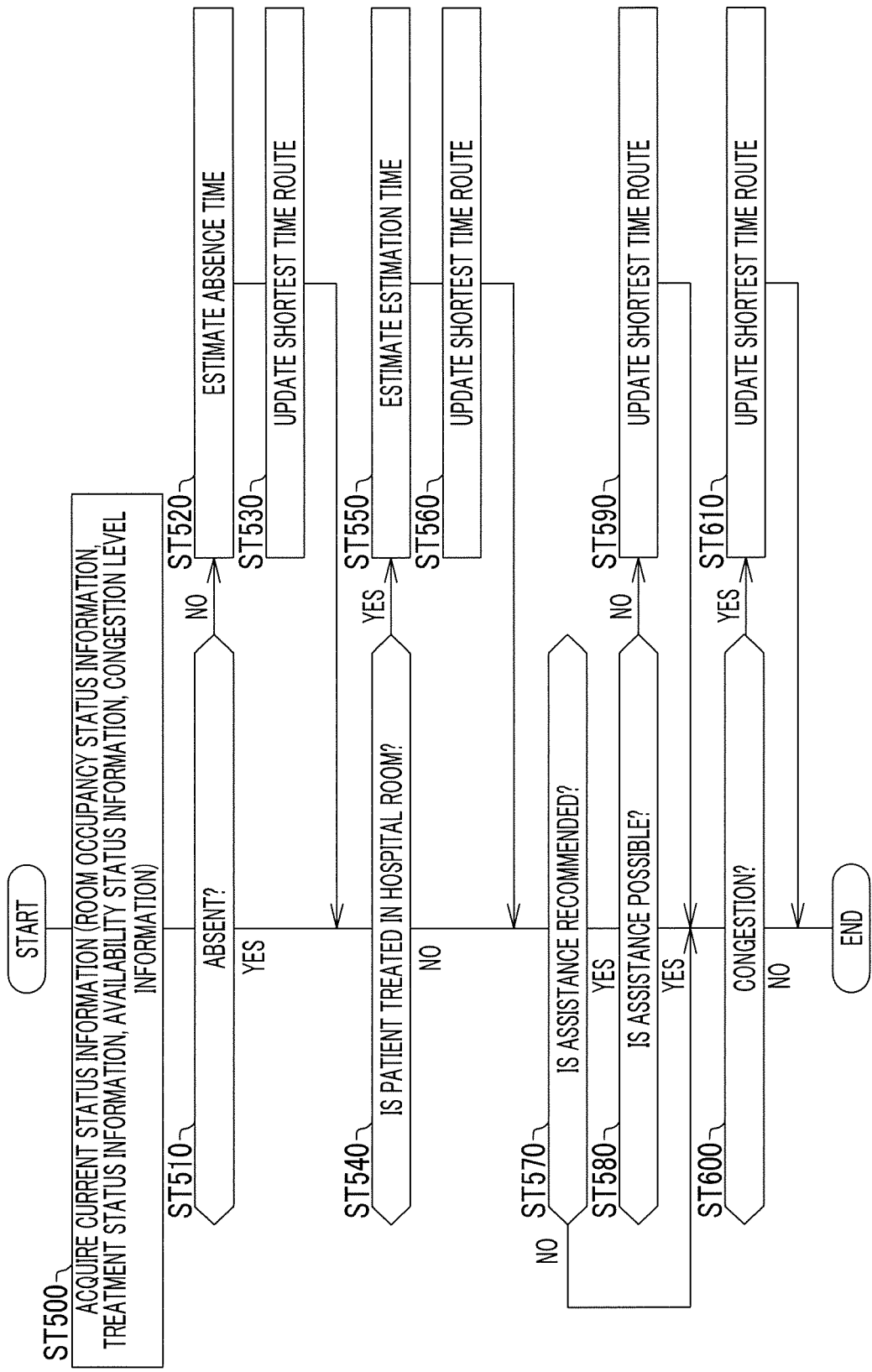
FIG. 37 is a flowchart showing a processing procedure of the rounding imaging management apparatus in a case where the fifth embodiment to the eighth embodiment are executed in combination.

FIG. 37 is a flowchart showing a processing procedure of the rounding imaging management apparatus 10 in a case where the fifth to eighth embodiments are combined. In this case, for example, the current status information 91 including the room occupancy status information 92, the treatment status information 100, the availability status information 110, and the congestion level information 115 is acquired by the fifth acquisition unit 90 (step ST500). In a case where the room occupancy status information 92 indicates that the patient P for whom rounding imaging is to be performed is absent (NO in step ST510), the absence time TA of the patient P indicated as being absent in the room occupancy status information 92 by the first estimation unit 93 is estimated (step ST520). Further, the updating unit 96 sets the shortest time route RST as the updated shortest time route RST_UD on the basis of the absence time TA (step ST530).

Next, in a case where the treatment status information 100 indicates that the patient P for whom rounding imaging is to be performed is treated in the hospital room 12 (YES in step ST540), the treatment time TM to be taken for the treatment in a case where the treatment status information 100 indicates that the patient P is treated in the hospital room 12 is estimated by the second estimation unit 101 (step ST550). Then, the updating unit 96 sets the shortest time route RST as the updated shortest time route RST_UD on the basis of the treatment time TM (step ST560).

Subsequently, in a case where in radiography recommended for assistance, the availability status information 110 indicates that the assistant AS scheduled to perform assistance is indicated as being unable to perform assistance (YES in step ST570, and NO in step ST580), the updating unit 96 sets the shortest time route RST as the updated shortest time route RST_UD on the basis of the availability status information 110 (step ST590).

Further, in a case where there is a place where the congestion level is "high" in the congestion level information 115 and there is a route passing through the place where the congestion level is "high" in the shortest time route RST (YES in step ST600), the updating unit 96 sets the shortest time route RST as the updated shortest time route RST_UD on the basis of the congestion level information 115 (step ST610). As described above, in a case where the fifth to eighth embodiments are executed in combination, it is possible to more smoothly advance rounding imaging.

Ninth Embodiment

In a ninth embodiment shown in FIGS. 38 to 41, in a case where an actual total necessary time that is a total necessary time in a case where rounding imaging is actually performed according to the rounding plan 16 is delayed by a set time or longer from a predicted total necessary time TF, delay cause information 121 indicating a cause of the delay of the actual total necessary time is received, the delay cause information 121 is recorded in the storage unit.

Figure 38:
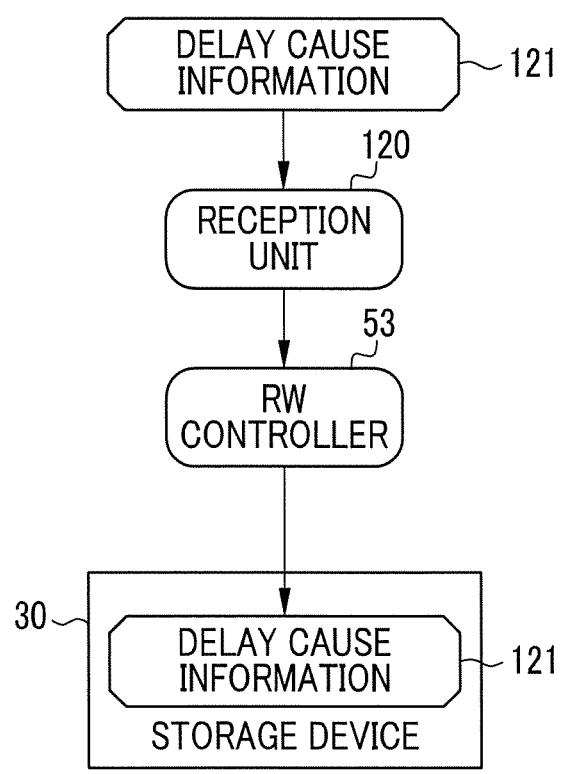
FIG. 38 is a diagram showing a ninth embodiment in which delay cause information indicating a cause of delay in an actual total necessary time is received and the delay cause information is recorded in a storage unit.

In FIG. 38, a reception unit 120 receives the delay cause information 121 indicating the cause of the delay of the actual total necessary time. The reception unit 120 outputs the received delay cause information 121 to the RW controller 53. The RW controller 53 performs a control for recording the delay cause information 121 from the reception unit 120 in the storage device 30. That is, the RW controller 53 is an example of a "recording controller" according to the technique of the present disclosure. Further, the storage device 30 is an example of a "storage unit" according to the technique of the present disclosure.

The output controller 54 performs a control for outputting a delay cause input screen 125 shown in FIG. 39 to the mobile radiography apparatus 11 in a case where the actual total necessary time is delayed by a set time or longer from the predicted total necessary time TF. The reception unit 120 receives the delay cause information 121 input through the delay cause input screen 125. The actual total necessary time is obtained by measuring a timing from when leaves the preparation room 17 to when the mobile radiography apparatus 11 returns to the preparation room 17. Further, the set time is 10 minutes, for example.

On the delay cause input screen 125, a message 126 for prompting the operator OP to input the delay cause information 121, a pull-down menu 127 for selecting a main cause, a pull-down menu 128 for selecting an occurrence location, and a pull-down menu 129 for selecting an occurrence time slot, or the like, are displayed. Options for main causes include facility construction, device malfunction, and the like. In a case where the device malfunction is selected, a pull-down menu for selecting a device causing the malfunction appears on the delay cause input screen 125. Options of the occurrence location include the entire floors such as the second floor and the third floor, in addition to individual places such as the preparation room 17 and the hallway A2 shown in the figure. Options of the occurrence time slot include morning, afternoon, all day, and the like, in addition to time slots shown in the figure.

In a case where the main cause, the occurrence location, the occurrence time slot, and the like are selected in the pull-down menus 127 to 129, or the like and an OK button 130 is selected, the reception unit 120 receives the delay cause information 121 including the main cause, the occurrence location, the occurrence time slot, and the like selected in the pull-down menus 127 to 129.

As described above, in the ninth embodiment, in a case where the actual total necessary time in a case where rounding imaging is actually performed according to the rounding plan 16 is delayed by the set time or longer from the predicted total necessary time TF, the reception unit 120 receives the delay cause information 121 indicating the cause of delay of the actual total necessary time. The RW controller 53 records the delay cause information 121 in the storage device 30. Accordingly, the delay cause information 121 may be reflected in creation of the rounding route R.

Figure 40:
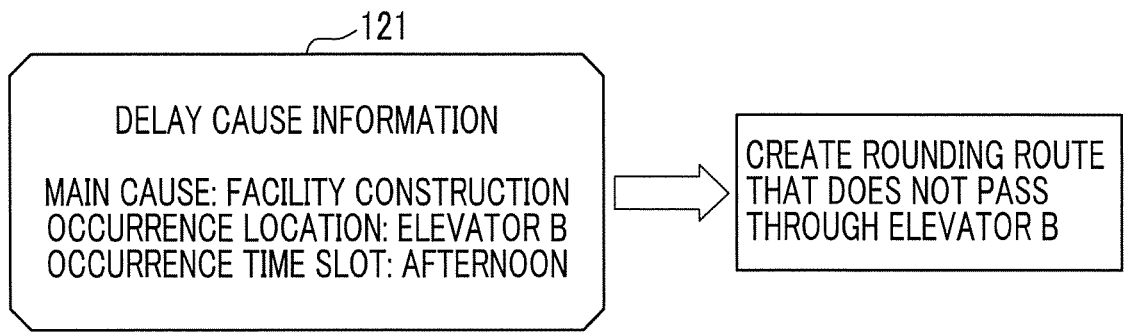
FIG. 40 is a diagram for illustrating an effect of the ninth embodiment.

For example, as shown in FIG. 40, a case where the delay cause information 121 indicating that the main cause is "facility construction", the occurrence location is "elevator B", and the occurrence time slot is "afternoon" is stored in the storage device 30 is considered. In this case, as shown on a right side of an arrow, the creation unit 51 creates a rounding route R that does not pass through the elevator B in the afternoon.

Figure 41:
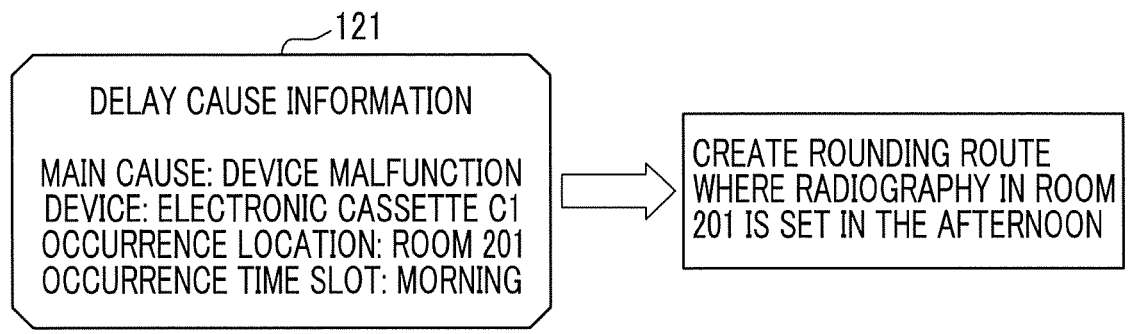
FIG. 41 is a diagram for illustrating an effect of the ninth embodiment.

Further, for example, as shown in FIG. 41, a case where the delay cause information 121 indicating that the main cause is "device malfunction", the device is an "electronic cassette C1", the occurrence location is the "room 201", and the occurrence time slot is "morning" is stored in the storage device 30 is considered. In this case, as shown on a right side of an arrow, the creation unit 51 creates a rounding route R where the radiography of the room 201 is performed in the afternoon. Since the rounding imaging is possible based on a more actual situation, it is possible to avoid a situation in which the actual total necessary time is delayed by the set time or longer from the predicted total necessary time TF.

The delay cause information 121 is erased from the storage unit by an hand of the operator OP or the like in a case where the cause is removed due to completion of a facility work or repair of an electronic cassette, for example.

Specific examples of the device malfunction include malfunction of the electronic cassette due to strong magnetic field noise generated from an MRI examination room, disruption of wireless communication between the electronic cassette and the mobile radiography apparatus 11 due to time-dependent radio interference, destabilization of console software of the mobile radiography apparatus 11, or the like. It is preferable that a device in which the malfunction has occurred is not used from the next rounding imaging and manufacturer's maintenance service is requested for repair.

The necessary time T in the rounding imaging in a case where the delay cause information 121 is received by the reception unit 120 may not be registered in the time results data 15 as an irregular value. Further, the delay cause input screen 125 may be displayed on the display 34 of the rounding imaging management apparatus 10, and the delay cause information 121 may be input through the input device 35.

Tenth Embodiment

Figure 42:
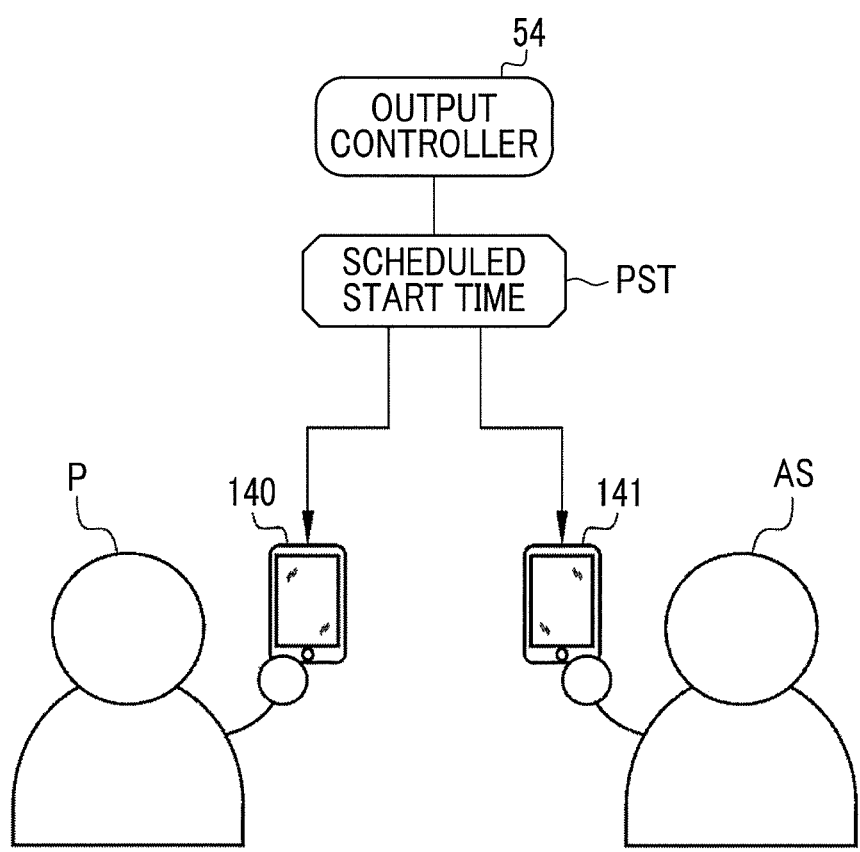
FIG. 42 is a diagram showing a tenth embodiment in which a scheduled start time of radiography according to a rounding plan is output.

In a tenth embodiment shown in FIGS. 42 and 43, the scheduled start time PST of radiography according to the rounding plan 16 is output.

As shown in FIG. 42, the output controller 54 performs a control for outputting the scheduled start time PST of radiography according to the rounding plan 16 to the portable terminal 140 of the patient P and the portable terminal 141 of the assistant AS. Specifically, the output controller 54 outputs the scheduled start time PST in the form of a scheduled start time display screen 150 shown in FIG. 43.

Figure 43A:
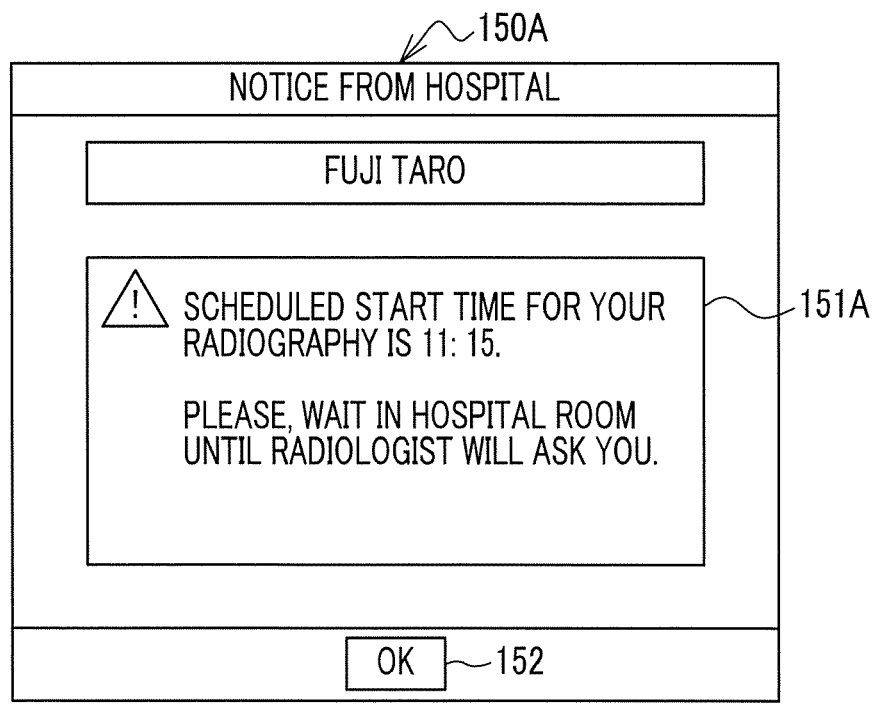

A scheduled start time display screen 150A shown in FIG. 43A is a screen that is output to the portable terminal 140 of the patient P. A message 151A for notifying the patient P of the scheduled start time PST of radiography is displayed on the scheduled start time display screen 150A.

Figure 43B:
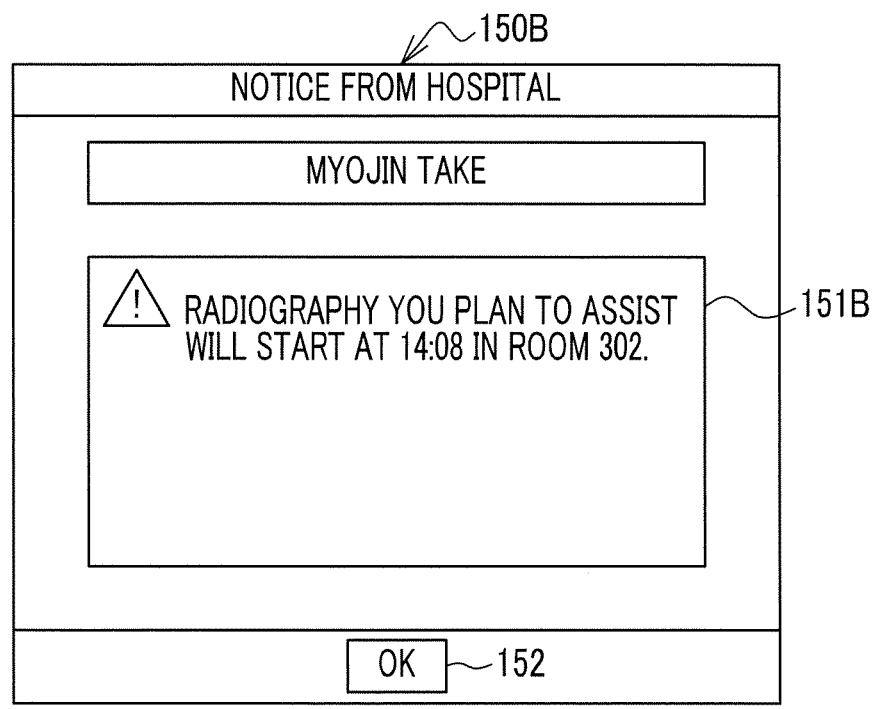

On the other hand, a scheduled start time display screen 150B shown in FIG. 43B is a screen that is output to the portable terminal 141 of the assistant AS. A message 151B for notifying the assistant AS of the scheduled start time PST of radiography and the hospital room 12 is displayed on the scheduled start time display screen 150B. An OK button 152 is a button for turning off the display of the scheduled start time display screen 150.

As described above, in the tenth embodiment, the output controller 54 performs a control for outputting the scheduled start time PST of radiography according to the rounding plan 16. Accordingly, it is possible to prevent in advance a situation that prevents the progress of rounding imaging such as absence of the patient P in the hospital room 12 at the scheduled start time PST, or non-arrival of the assistant AS at the hospital room 12 at the scheduled start time PST of radiography recommended for assistance. As a result, it is possible to smoothly perform rounding imaging.

A timing at which the scheduled start time display screen 150 is output is preferably closer to the scheduled start time PST, such as 10 minutes before the scheduled start time PST, since a reminder effect is high.

It is sufficient if the rounding plan 16 includes any one of the rounding route R and the predicted total necessary time TF. Further, an output form of the rounding plan 16 by the output controller 54 is not limited to the exemplified rounding plan display screen 65. The rounding plan 16 may be printed out, or may be output as a file. This is similarly applied to an output form of the scheduled start time PST.

In a case where there is radiography that needs a jig such as a radiation marker or a positioning aid, a message indicating that the jig is necessary may be displayed on the rounding route R on the rounding plan display screen 65.

Instead of or in addition to the movement time TT, a movement speed of the mobile radiography apparatus 11 may also be recorded. As a method for calculating the movement speed, for example, the amount of rotation of a motor that moves the mobile radiography apparatus 11 is measured by a rotary encoder, and a movement distance of the mobile radiography apparatus 11 is obtained from the measurement result. Then, the obtained movement distance is divided by the movement time TT. In a case where the movement speed is recorded, the congestion level of the hospital may be derived from the movement speed, such as "low" in a place where the movement speed is relatively fast and "high" in a place where the movement speed is relatively slow.

Various modifications may be made to a hardware configuration of a computer that configures the rounding imaging management apparatus 10. For example, the rounding imaging management apparatus 10 may be configured by a plurality of computers separated as hardware for the purpose of improving processing capability or reliability. Specifically, the functions of the first acquisition unit 50 and the creation unit 51, the functions of the second acquisition unit 52 and the output controller 54, and the function of the RW controller 53 may be distributed to three computers. In this case, the rounding imaging management apparatus 10 is configured by three computers.

As described above, the hardware configuration of the computer may be appropriately changed according to necessary performance such as processing capability, safety, and reliability. Further, not only the hardware but also an application program such as the operating program 40 may be duplicated, or may be dividedly stored in a plurality of storage devices for the purpose of securing safety or reliability.

In each of the above embodiments, the rounding imaging management apparatus 10 has been described as an example of an "recording apparatus" according to the technique of the present disclosure, but the functions of the recording apparatus may be performed by another apparatus other than the rounding imaging management apparatus 10. Further, the mobile radiography apparatus 11 may serve as the functions of the rounding imaging management apparatus 10 and the recording apparatus.

In the above embodiments, for example, as a hardware structure of processing units that executes a variety of processes, such as the first acquisition unit 50, the creation unit 51, the second acquisition unit 52, the RW controller 53, the output controller 54, the third acquisition unit 75, the fourth acquisition unit 80, the fifth acquisition unit 90, the first estimation unit 93, the updating unit 96, the second estimation unit 101, and the reception unit 120, the following various processors may be used. The various processors may include a CPU that is a general-purpose processor that executes software and functions as a variety of processing units, a programmable logic device (PLD) of which a circuit configuration is changeable after manufacturing, such as a field-programmable gate array (FPGA), a dedicated electric circuit that is a processor having a circuit configuration that is exclusively designed to execute a specific process, such as an application specific integrated circuit (ASIC), or the like.

Further, one processing unit may be configured by one processor among the variety of processors described above, or may be configured by a combination of two or more processors of the same type or different types (for example, a combination of a plurality of FPGAs or a combination of a CPU and an FPGA). In addition, a plurality of processing units may be configured by one processor.

As an example in which a plurality of processing units are configured by one processor, first, as represented by a computer such as a client or a server, a configuration in which a combination of one or more CPUs and software forms one processor and this processor functions as a plurality of processing units may be employed. Second, as represented by a system on chip (SoC) or the like, a configuration in which a processor for realizing entire functions of a system including a plurality of processing units using one integrated circuit (IC) chip is used may be employed. In this way, the variety of processing units may be configured by using one or more of the variety of processors as the hardware structure.

Further, the hardware structure of the variety of processors is, more specifically, electric circuitry in which circuit elements such as semiconductors are combined.

From the above description, the invention disclosed in the following appendix 1 may be understood.

[Appendix 1] A rounding imaging management apparatus that manages rounding imaging for radiographing individual patients while rounding hospital rooms using a mobile radiography apparatus, comprising: a first acquiring processor that acquires imaging order information indicating content of the radiography in the rounding imaging to be performed; a second acquiring processor that acquires, from time results data in which a necessary time in the rounding imaging performed in the past is registered, the necessary time; a creating processor that creates a rounding plan of the rounding imaging on the basis of the imaging order information and the necessary time; and an output controlling processor that performs a control for outputting the rounding plan.

The technique of the present disclosure may be made by appropriately combining the above-described various embodiments and various modification examples. Further, the invention is not limited to the above embodiments, and various configurations may be employed without departing from the concept of the present invention. In addition, the technique of the present disclosure extends to a storage medium that non-temporarily stores a program, in addition to the program.

The above-described content and the above-illustrated content are detailed descriptions of partial examples related to the technique of the present disclosure, which are merely examples of the technique of the present disclosure. For example, the above description related to the configurations, functions, operations, and effects is an explanation related to an example of the configurations, functions, operations, and effects of partial examples according to the technique of the present disclosure. Accordingly, it is needless to say that an unnecessary portion may be deleted, or a new element may be added or replaced with respect to the above-described content and the above-illustrated content without departing from the scope of the technique of the present disclosure. In addition, in order to avoid complication and facilitate understanding of partial examples related to the technique of the present disclosure, in the above-described content and the above-illustrated content, explanation about technical common sense that does not need any particular explanation is omitted.

In this specification, "A and/or B" is synonymous with "at least one of A or B". That is, "A and/or B" includes three cases of only A, only B, and a combination of A and B. Further, in this specification, the same concept as "A and/or B" is also applied to a case where three or more things are expressed by connecting them with "and/or".

All documents, patent applications, and technical standards disclosed in this specification are incorporated by reference in this specification to the same extent as if each individual document, patent application and technical standard were specifically and individually stated to be incorporated by reference.

What is claimed is:

1. A rounding imaging management apparatus that manages rounding imaging for radiographing individual patients while rounding hospital rooms using a mobile radiography apparatus, comprising:
 a first acquisition unit that acquires imaging order information indicating content of the radiography in the rounding imaging to be performed;
 a second acquisition unit that acquires, from time results data in which a necessary time in the rounding imaging performed in the past is registered, the necessary time;
 a creation unit that creates a rounding plan of the rounding imaging on the basis of the imaging order information and the necessary time; and
 an output controller that performs a control for outputting the rounding plan.

2. The rounding imaging management apparatus according to claim 1,
 wherein the rounding plan includes a rounding route of the mobile radiography apparatus.

3. The rounding imaging management apparatus according to claim 2,
 wherein an individual necessary time taken for each past radiography is registered as the necessary time in the time results data,
 wherein the second acquisition unit acquires the individual necessary time corresponding to the radiography indicated by the imaging order information, and
 wherein the rounding plan includes a predicted total necessary time that is calculated on the basis of the individual necessary time and predicted to be taken for the entire rounding imaging.

4. The rounding imaging management apparatus according to claim 3,
 wherein the individual necessary time is at least one of an imaging time of the radiography or a movement time of the mobile radiography apparatus, and
 wherein the time results data is at least one of imaging time results data in which the imaging time is registered or movement time results data in which the movement time is registered.

5. The rounding imaging management apparatus according to claim 3,
 wherein the imaging time results data is data in which a time slot and the individual necessary time are registered in association with each other, and the individual necessary time varies according to the time slot, and
 wherein the creation unit creates a shortest time route where the predicted total necessary time becomes the shortest as the rounding route.

6. The rounding imaging management apparatus according to claim 5,
 wherein the imaging order information includes hospital room information of the hospital room of the patient for whom the rounding imaging is to be performed, and
 wherein the creation unit creates a shortest distance route where a movement distance of the mobile radiography apparatus becomes the shortest on the basis of the hospital room information, and then, corrects the shortest distance route in accordance with the individual necessary time to create the shortest time route.

7. The rounding imaging management apparatus according to claim 5, further comprising:
 a third acquisition unit that acquires patient schedule information in which a schedule of treatment for the patient is registered,
 wherein the creation unit creates the shortest time route with reference to the patient schedule information.

8. The rounding imaging management apparatus according to claim 5, further comprising:
 a fourth acquisition unit that acquires assistant schedule information in which a schedule of an assistant who assists the radiography is registered,
 wherein the creation unit creates the shortest time route with reference to the assistant schedule information.

9. The rounding imaging management apparatus according to claim 5, further comprising:
 a fifth acquisition unit that acquires current status information indicating a current status of information that is a source of creation of the rounding plan during the rounding imaging based on the shortest time route; and
 an updating unit that updates the shortest time route and sets the updated shortest time route in a case where the current status information includes content which changes the individual necessary time,
 wherein the output controller outputs the updated shortest time route.

10. The rounding imaging management apparatus according to claim 9,
 wherein the current status information is at least one of room occupancy status information indicating a room occupancy status in the hospital room of the patient for whom the rounding imaging is to be performed, treatment status information indicating a status of treatment in the hospital room of the patient for whom the rounding imaging is to be performed, availability status information indicating an availability status of an assistant who assists the radiography, or congestion level information indicating a congestion level of a hospital.

11. The rounding imaging management apparatus according to claim 10, further comprising:
 a first estimation unit that estimates an absence time of the patient indicated as being absent in the room occupancy status information,
 wherein the updating unit updates the shortest time route on the basis of the absence time estimated by the first estimation unit.

12. The rounding imaging management apparatus according to claim 10, further comprising:
 a second estimation unit that estimates, in a case where the treatment status information indicates that the treatment is performed in the hospital room, a treatment time to be taken for the treatment,
 wherein the updating unit updates the shortest time route on the basis of the treatment time estimated by the second estimation unit.

13. The rounding imaging management apparatus according to claim 3, comprising:

a reception unit that receives, in a case where an actual total necessary time in a case where the rounding imaging is actually performed in accordance with the rounding plan is delayed by a set time or longer from the predicted total necessary time, delay cause information indicating a cause of the delay of the actual total necessary time; and a recording controller that performs a control for recording the delay cause information in a storage unit.

14. The rounding imaging management apparatus according to claim 1, wherein the output controller performs a control for outputting a scheduled start time of the radiography based on the rounding plan.

15. The rounding imaging management apparatus according to claim 1, further comprising a recording controller that records the necessary time in the rounding imaging performed in the past is stored in a storage unit, in order to manage the rounding imaging for radiographing the individual patients while rounding the hospital rooms using the mobile radiography apparatus.

16. A method for operating a rounding imaging management apparatus that manages rounding imaging for radiographing individual patients while rounding hospital rooms using a mobile radiography apparatus, comprising:

acquiring imaging order information indicating content of the radiography in the rounding imaging to be performed;

acquiring, from time results data in which a necessary time in the rounding imaging performed in the past is registered, the necessary time;

creating a rounding plan of the rounding imaging on the basis of the imaging order information and the necessary time; and performing a control for outputting the rounding plan.

17. A non-transitory computer-readable storage medium storing a program for operating rounding imaging management apparatus that manages rounding imaging for radiographing individual patients while rounding hospital rooms using a mobile radiography apparatus, the program causing a computer to function as:

a first acquisition unit that acquires imaging order information indicating content of the radiography in the rounding imaging to be performed;

a second acquisition unit that acquires, from time results data in which a necessary time in the rounding imaging performed in the past is registered, the necessary time;

a creation unit that creates a rounding plan of the rounding imaging on the basis of the imaging order information and the necessary time; and an output controller that performs a control for outputting the rounding plan.

18. The non-transitory computer-readable storage medium according to claim 17, further storing a data structure in which the necessary time in the rounding imaging performed in the past is registered, in order to manage the rounding imaging for radiographing the individual patients while rounding the hospital rooms using the mobile radiography apparatus.

* * * * *